(12) United States Patent
Pascal et al.

(10) Patent No.: US 6,191,292 B1
(45) Date of Patent: Feb. 20, 2001

(54) PRECURSORS OF THE A-RING OF VITAMIN D AND METHOD AND INTERMEDIATES FOR THE PREPARATION THEREOF

(75) Inventors: Jean-Claude Pascal, Nice (FR); Maurits Vandewalle, Ghent (BE); Philippe Maillos, Nice (FR); Pierre De Clercq, Ghent (BE)

(73) Assignee: Laboratoire Theramex (MC)

( * ) Notice: Under 35 U.S.C. 154(b), the term of this patent shall be extended for 0 days.

(21) Appl. No.: 09/456,509

(22) Filed: Dec. 8, 1999

(51) Int. Cl.[7] .................... C07C 401/00; C07C 403/00; C07D 315/00; C07D 307/02; C07F 7/00

(52) U.S. Cl. .................. 552/653; 552/653; 549/214; 549/426; 549/427; 549/493; 549/497; 549/498; 549/502; 556/413; 556/465; 560/1; 560/125; 562/507; 562/508

(58) Field of Search .................... 549/214, 426, 549/427, 493, 497, 498, 502; 556/413, 465; 560/1, 125; 562/507, 508; 564/191, 123; 558/234, 235; 568/20, 374, 445; 552/653

(56) References Cited

U.S. PATENT DOCUMENTS 6,017,907   1/2000   Bouillon et al. .................... 514/167

OTHER PUBLICATIONS

Sheng–Ze Zhou et al, "A Practical Synthesis of A–ring Precursors . . . ", Tetrahedron Lett., 1996, pp. 7637–7640, XP–004068868.

Yong, Wu et al, "A new A–ring Precursor for 19–nor–1. α. . . ", Synlett (1996), pp. 911–912. XP–002134811.

Wang et al, "Model Studies of the Stereoelectronic Effect in RH (II) . . . ", J.Am. Chem. Soc., (1994), pp. 3296–3305, XP–002134812.

Huang et al, "A Novel Synthesis of 19–Nor 1α, 25–dihydroxyvitamin $D_3$ . . . ", Tetrahedron Lett., pp. 8299–8302 (1995), vol. 36, No. 45.

*Primary Examiner*—Sabiha N. Qazi
(74) *Attorney, Agent, or Firm*—Dennison, Scheiner, Schultz & Wakeman

(57) ABSTRACT

The invention relates to precursors of the A-ring of vitamin D, of the formula (I):

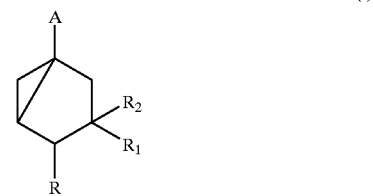

in which A, R, $R_1$ and $R_2$ are as defined in the specification.

The invention also relates to a method of preparing compounds (I) comprising the enzymatic asymmetrization of 3,5-dihydroxybenzoic acid derivatives, as well as intermediates of preparation of said compounds.

9 Claims, No Drawings

PRECURSORS OF THE A-RING OF VITAMIN D AND METHOD AND INTERMEDIATES FOR THE PREPARATION THEREOF

BACKGROUND OF THE INVENTION

This invention discloses precursors that can be used effectively for the synthesis of 19-nor-vitamin D analogues, as well as a method and intermediates for the preparation thereof. More specifically, the invention relates to precursors of the A-ring of said vitamin D analogues, which A-ring is represented by the structure below

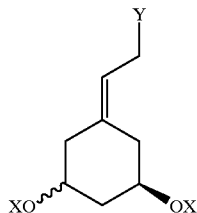

(see for instance Mazur et al., *Tetrahedron Letters* 1995, 2987).

The synthesis of bicyclo[3.1.0]hexane derivatives, as 19-nor- A-ring precursors has been developed from (−)-quinic acid or cyclohexane-triol by M. Vandewalle et al. (*Tetrahedron Letters*, 1995, 36 (45), 8299–8302) and is based on the well-known sigmatropic rearrangement of cyclopropylic alcohol into homoallylic alcohol. The potential of this rearrangement in natural vitamin D has been first demonstrated by Mazur et al. (op. cit.). An alternative synthesis from 2,4-pentane-dione was also reported (S. Z. Zhou, S. Anne, M. Vandewalle, *Tetrahedron Letters*, 1996, 37 (42), 7637–7640). 3-Cyclopentenol was also used as a precursor for this preparation (W. Yong, M. Vandewalle; *Synlett*, 1996, 9, 911–912).

These methods however present the following disadvantages:

- The preparation from (−)-quinic acid involves a radicalar desoxygenation which is difficult to control on large quantity, and the use of toxic tributltinhydride;
- The process from cyclohexane triol is conducted via a large number of steps (12) and needs two enzymatic reactions;
- The starting material, 3-cyclopentenol is not commercially available. It must be prepared from cyclopentadiene via a low yielding (30%) hydroboration step. Furthermore the cyclopropanation and the introduction of the formyl group are cumbersome;
- The synthesis starting from 2,4-pentane dione (10 steps) suffers from low yields in the first step for preparing the intermediate bis epoxide. Furthermore, due to their low molecular weight some intermediates are rather volatile and difficult to purify in a large scale process.

SUMMARY OF THE INVENTION

It has now been found that a broad range of 19-nor-A-ring precursors can be prepared starting from 3,5-dihydroxybenzoic acid derivatives or their 4-alkyl substituted homologues. These precursors can be obtained on a large scale by a method which is more efficient than previously disclosed methods.

Thus, according to a first feature, the invention relates to a method of preparing a compound of formula (I):

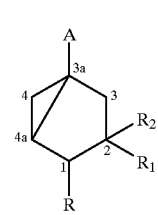

(I)

in which:

A is a group —$CH_2OH$, —$CH_2$—$OCOR'$, —$COR''$, —$CSR''$ or an ethynyl;

R is hydrogen or a ($C_1$–$C_6$)alkyl;

$R_1$ is hydrogen, a ($C_1$–$C_6$)alkyl or a group —$(CH_2)_n$—OP;

$R_2$ is hydrogen or a group —OP;

R' is a ($C_1$–$C_6$)alkyl or a phenyl;

R'' is hydrogen, a hydroxyl, a ($C_1$–$C_6$)alkyl, a ($C_1$–$C_6$)alkoxy, a ($C_1$—$C_6$)alkylthio, or a di($C_1$–$C_3$)alkylamino;

P is hydrogen; a ($C_1$–$C_6$)alkanoyl; a benzoyl in which the phenyl is optionally substituted by a ($C_1$–$C_4$)alkyl, a halogen or a nitro; a ($C_1$–$C_6$)alkoxycarbonyl; a group —$Si(R_3)_3$ in which each $R_3$ independently represents a ($C_1$–$C_6$)alkyl or a phenyl; a mono- or di-($C_1$–$C_6$)alkoxy ($C_1$–$C_6$)alkyl; a tetrahydrofuranyl; or a tetrahydropyranyl;

n is 0, 1, 2, 3 or 4, preferably 0 or 1, which method comprises the steps of (i) reacting a compound of formula 1

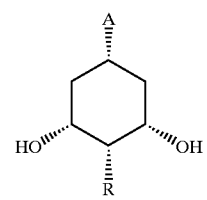

1 in which A is a ($C_1$–$C_6$)alkoxycarbonyl, preferably a methoxycarbonyl, or a di($C_1$–$C_3$)alkylaminocarbonyl and R is as defined above, with a lipase in a vinylalkanoate or an acid anhydride, and (ii) converting the resulting compound of formula 2 or 2'

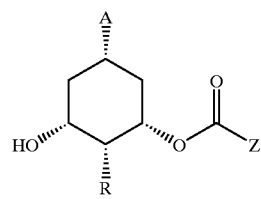

2

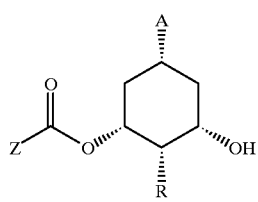

in which Z is an alkyl such as a ($C_1$–$C_6$)alkyl, preferably a ($C_1$–$C_3$)alkyl to the corresponding compound of formula (I).

DETAILED DESCRIPTION OF THE INVENTION

As shown in general scheme 1, the starting material for the preparation of the A-ring precursors is obtained by hydrogenation of a methyl 3,5-dihydroxybenzoic acid or an ester thereof or of their 4-alkyl substituted homologues following a modified procedure from that described by P. Wang and J. Adams in *J. Am Chem Soc* 1994, 116, 3296–3305.

The first step comprises the enzyme catalyzed asymmetrisation of 1-alkoxy (or dialkylamino)carbonyl-3,5-dihydroxy-cyclohexane or its 4-alkyl-substituted homologues in a solvent such as a vinylalkanoate, for example vinylacetate, vinylpropionate or vinylbutyrate or an acid anhydride, for example acetic anhydride, propionic anhydride or butyric anhydride and using a lipase such as SAM II (lipase from *Pseudomonas fluorescens*), CCL (lipase from *Candida cylindracea*), PPL (lipase from porcine pancreas), PSL (lipase from *Pseudomonas cepacia*), GCL (lipase from *Gotrichum candidum*), at a temperature between 10 and 40° C., preferably 20° C., during 6 to 72 hours, which affords the corresponding alkyl (or dialkyl) (1S,3S,5R)-3-alkylcarbonyloxy-5-hydroxy or (1S,3S,4R,5R)-4-alkyl-3-alkylcarbonyloxy-5-hydroxy-cyclohexanecarboxylate (or carboxamide) 2 or the corresponding alkyl (or dialkyl) (1S,3S,5R)-5-alkylcarbonyloxy-3-hydroxy or (1S,3S,4R,5R)-4-alkyl-5-alkylcarbonyloxy-3-hydroxy-cyclohexanecarboxylate (or carboxamide) 2'.

Also, asymetrisation via an enantiotoposelective enzyme-catalysed hydrolysis of diesters 3 with an appropriate enzyme can take place to conduct to the same family of compounds.

Schemes 2 and 3 describe the synthesis of all diastereoisomers of general formula (I) with $R_1$=H and $R_2$=OP, from compounds 2 and 2' described in scheme 1.

As shown in these schemes, the conversion of compounds 2 or 2' to compounds (I) is carried out via one or several of each of the following steps which can be performed partially or totally in a varying order depending on the eventual diastereoisomer: (1) protection of hydroxy groups (P=TBDMS, TBDPS for example), (2) ester saponification, (3) inversion of a 3 or 5-hydroxy group, (4) formation of a leaving group (L=OTos, OBros, OMs for example), (5) base included ring closure to the desired bicyclo[3.1.0]hexane, (6) transformation of the carboalkoxy or carbamoyl function (A) to the desired substituent A.

Steps (2) and (4) are conventional reactions well known to those skilled in the art. Step (1) can be carried out according to *J. Am. Chem. Soc.* 1972, 94, 6190 or *Protective groups in Organic Synthesis*, T. W. Greene, John Wiley Sons, New York. Step (3) can be carried out according to *Synthesis* 1981, 1, or by a two-step process (elimination, hydroboration). Step (5) can be carried out according to *Tetrahedron Letters*, 1995, 36 (45), 8299–8302. Step (6) can be carried out according to *J. Gen. Chem. USSR* 1964, 34, 1021.

Scheme 2 specifically describes the synthesis of all diastereoisomers with a 3aS configuration (α oriented cyclopropyl ring).

Scheme 3 specifically describes the synthesis of all diastereoisomers with a 3aR configuration (β oriented cyclopropyl ring).

As shown in general Scheme 4, the 3a hydroxymethyl substituted bicyclo[3.1.0]hexane compounds (I) with R=H and A=$CH_2OH$ can also be useful for the synthesis of A-ring precursors for vitamin D analogues modified at C-1. This possibility is examplified from I.a (R=H, P=TBDPS, A=$CH_2OH$) via ketone 4.2 as a key intermediate. Grignard reaction (for example $R_1$=Me or Et) leads diastereoselectively to the tertiary alcohols I.i, with concomitant removal of the protecting ester function. On the other hand methylenation of 4.2 gives 4.3. The best result (68% yield) was obtained with the Lombardo procedure (*Tetrahedron Lett.*, 1982, 23, 4293). Alternatively Wittig or Tebbe reaction (*J. Org. Chem.*,1985, 50, 1212) gave respective yields of 39% and 54%.

Dihydroxylation of 4.3 affords the expected diol I.m. as the major product next to the epimer 4.4 (ratio 85:15, not shown). On the other hand, the hydroboration of 4.3 gives 2R and 2S hydroxymethyl compounds in a 75:25 ratio (73%). These epimeric alcohols were separated to give I.j and I.k after TBDPS ether formation (81%) and subsequent ester hydrolysis (81%). Mercury acetate mediated water addition on 4.3 leads to tertiary alcohol I.l next to I.i in a 75:25 ratio.

This new method of preparation of 19-nor A ring precursors from 3,5-dihydroxybenzoic acid derivatives is shortest than the method previously described. The practical importance of the above route mainly resides in the fact that the majority of the intermediates are crystalline and can be purified by crystallisation which is more easy on a larger scale that the traditional purification by chromatography on silica gel, and guarantees a high degree of enantiomeric purity.

Scheme 1
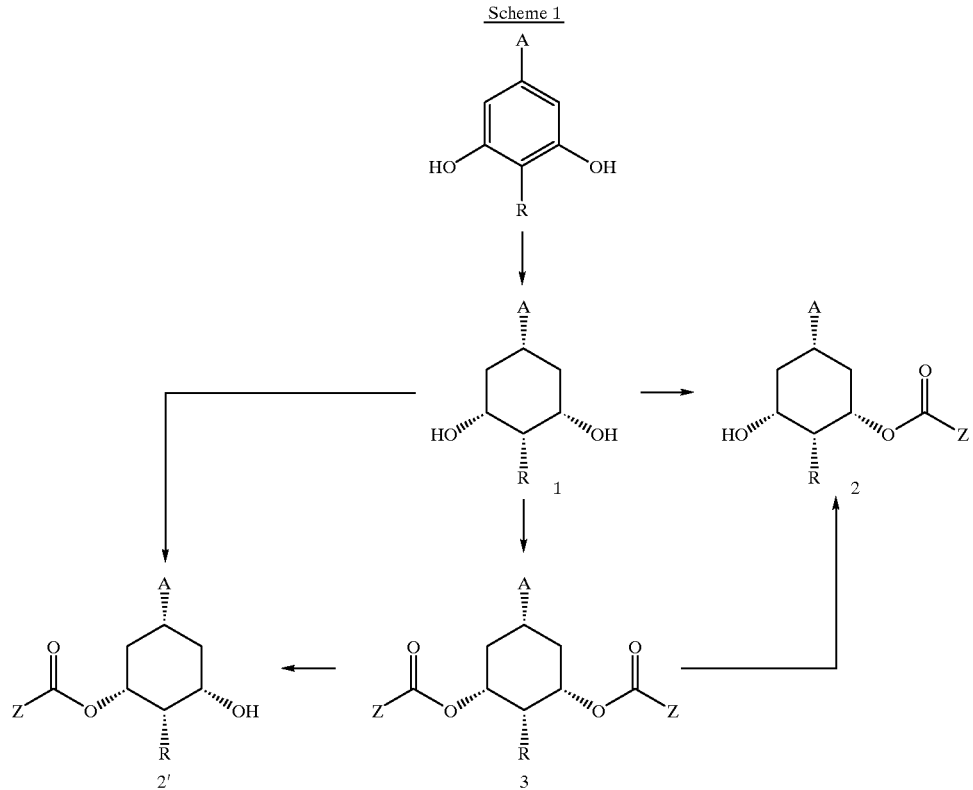
Scheme 2
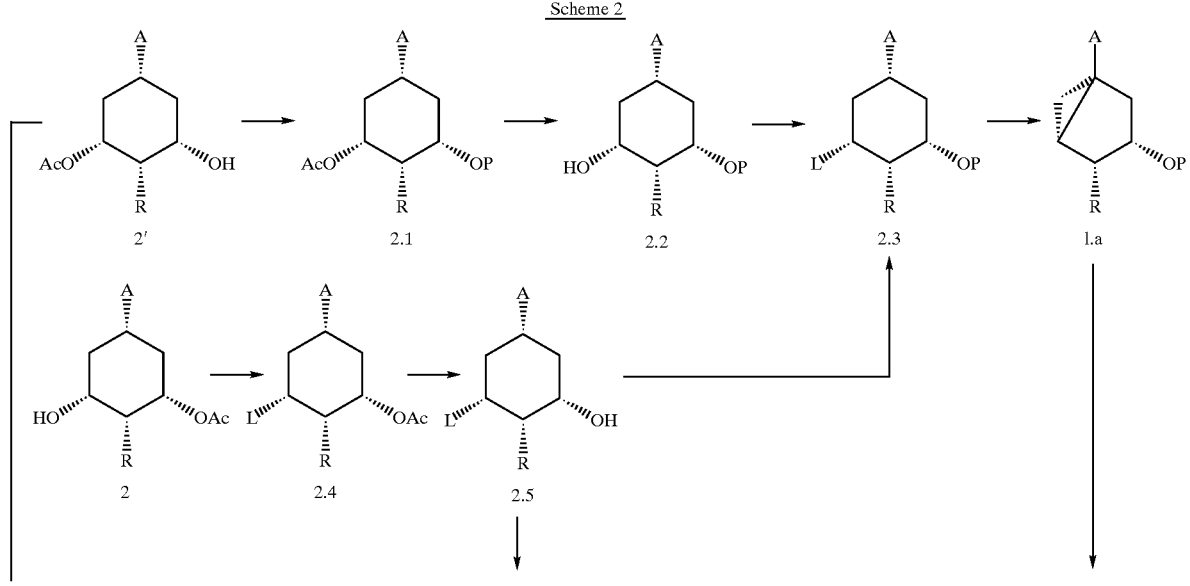

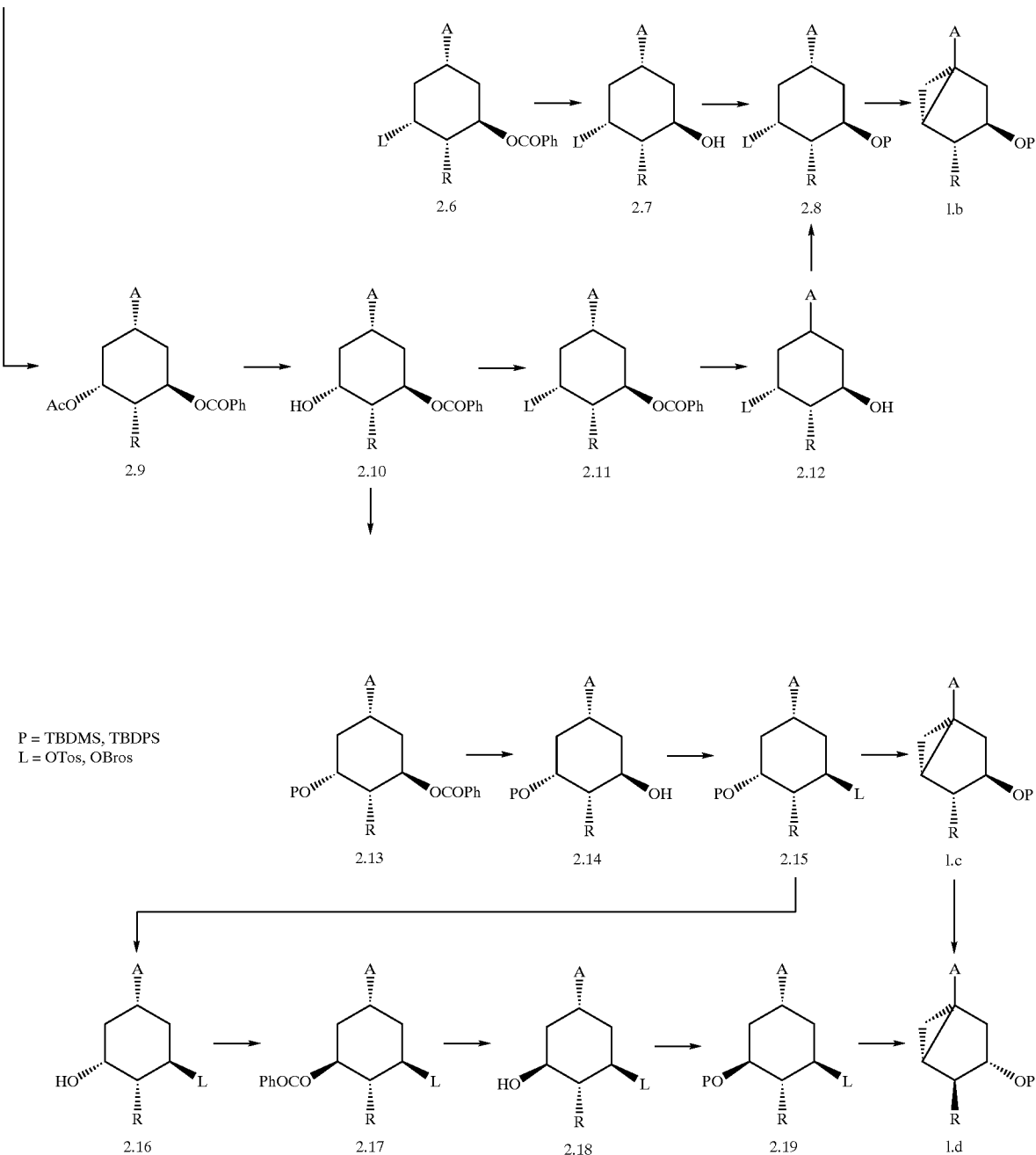
P = TBDMS, TBDPS
L = OTos, OBros

Scheme 3
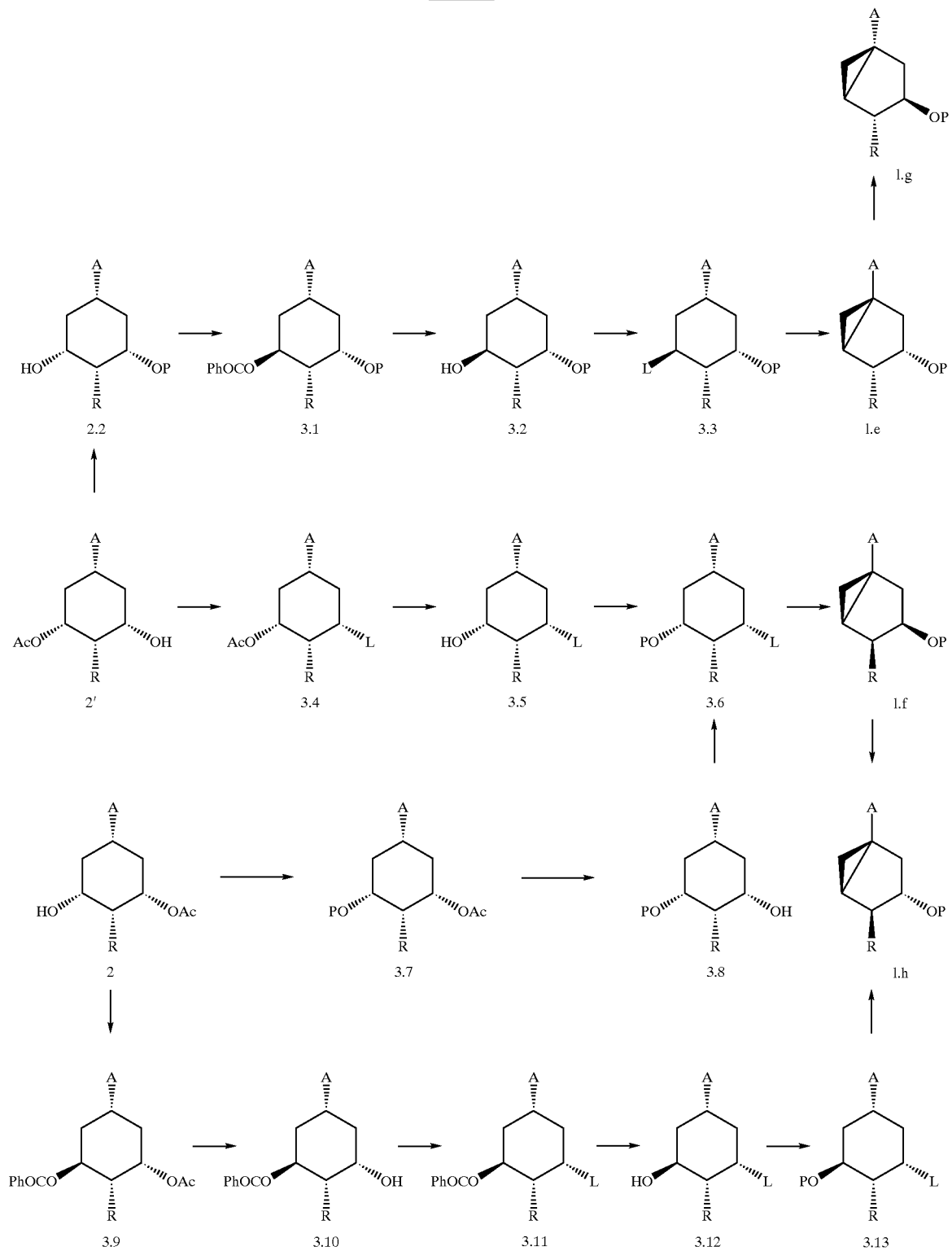
L = OTos, OBros, OMs
P = TBDMS, TBDPS

Scheme 4

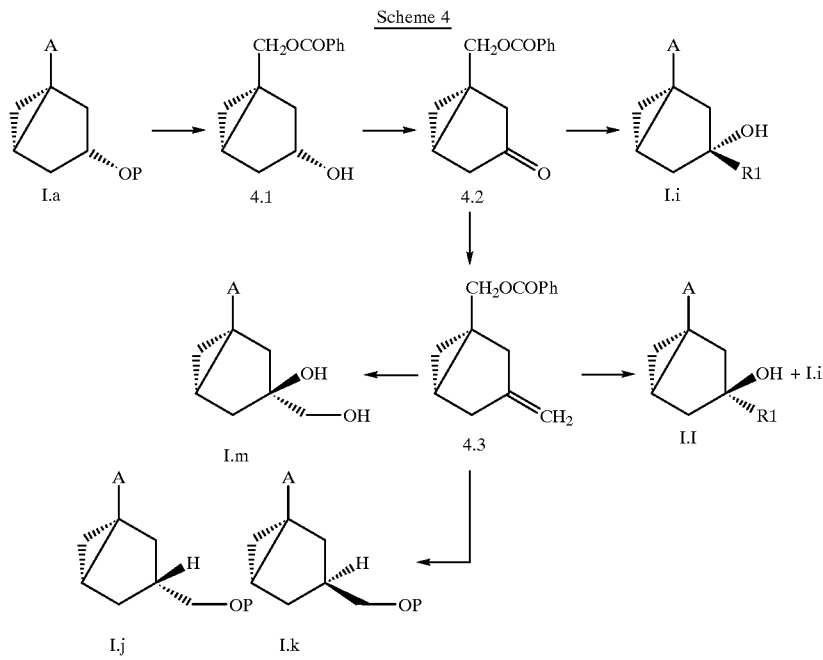

All of the compounds (I) thus prepared are novel except those of configuration 2S, 3aS, 4aS where A is a formyl, a hydroxymethyl, an ethynyl or a methoxycarbonyl, R and $R_2$ are both hydrogen and $R_1$ is a group —OSi($R_3$)$_3$.

These novel compounds therefore represent another feature of the invention.

Preferred compounds (I) include those where

A is a group —CH$_2$OH, —CH$_2$OCOR', —COR" or an ethynyl;

$R_1$ is a ($C_1$-$C_6$)alkyl or a group —(CH$_2$)$_n$—OP;

R' is a phenyl;

R" is hydrogen;

P is hydrogen or a group —Si($R_3$)$_3$;

n is 0 or 1.

The compounds (I) can be used for the synthesis of vitamin D (19-nor, 1α, 25(OH)$_2$-D$_3$) according for example to the following scheme as described in *Tetrahedron Letters*, 1996; 37 (42): 7637–7640:

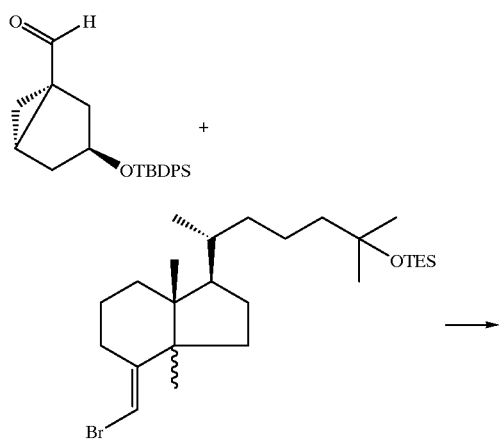

-continued

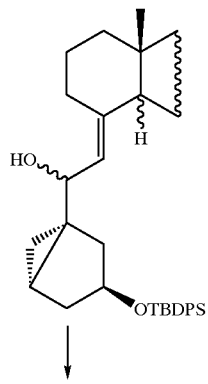

↓

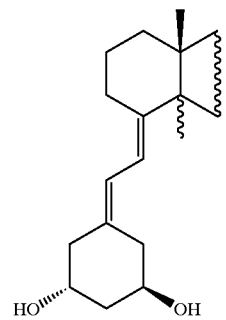

The invention further relates to the intermediates for the preparation of the compounds (I). Especially, the invention relates to the diastereoisomeric compound of formula (II):

(II)

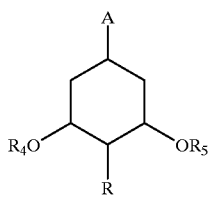

in which:
A and R are as defined above
$R_4$ and $R_5$ each independently represent a group P as defined above or a mesyl, tosyl, brosyl or trifluoromesyl group,
under the proviso that when A is a methoxycarbonyl and R is hydrogen the configuration of compound (II) is not 1R, 3R, 5R. Also within the scope of the invention are the compounds of formula 2 or 2'

2

2'

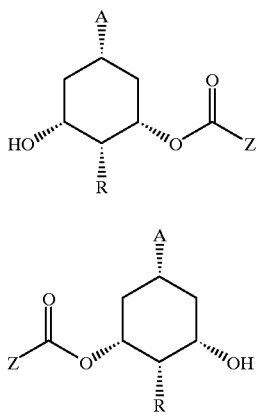

in which:
A and R are as defined above
Z is an alkyl,
as well as the compounds of formula 1

1

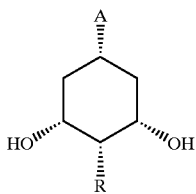

in which A is as defined above and R is a $(C_1-C_6)$alkyl.

In the present description and the appended claims, the term "$(C_1-C_3)$alkyl", "$(C_1-C_4)$alkyl" or "$(C_1-C_6)$alkyl" is understood as meaning a linear or branched hydrocarbon chain having 1 to 3 (respectively 4 or 6) carbon atoms such as for example a methyl, ethyl, propyl, isopropyl, butyl, isobutyl, tert-butyl, pentyl, isopentyl or hexyl radical.

The term "$(C_1-C_6)$alkoxy" or "$(C_1-C_6)$alkylthio" is understood as meaning a group OR or respectively SR in which R is a $(C_1-C_6)$alkyl as defined above.

The invention will now be illustrated by the following preparation and examples.

PREPARATION OF INTERMEDIATES OF FORMULA 1 a) cis,cis-3,5-Dihydroxy-1-(methoxycarbonyl)cyclohexane: 1.A (R=H, A=COOCH$_3$).

Methyl 3,5-dihydroxybenzoate was hydrogenated in MeOH in similar conditions as described by Peng Wang and Julian Adams in *J. Am. Chem. Soc.* 1994, 116, 3296–3305 for the hydrogenation of 3,5-dihydroxybenzoic acid.

Methyl 3,5-dihydroxybenzoate (57.6 g, 0.629 mol, 97%), 5% Rh/Al$_2$O$_3$ (5.76 g) in MeOH (400 ml) containing 0.1% of AcOH was added into an autoclave (1 L). The autoclave was steamed two times with hydrogen (from 130 atm. to 40 atm.). The hydrogen pressure reached 130 atm. and temperature was raised to 80–85° C. In the process of raising the temperature, the pressure of hydrogen decreased. When the pressure decreased to 90 atm. the hydrogen pressure was brought to 130 atm. again. The hydrogenation was carried out for 12 h at 80–85° C. and 130 atm., then the temperature was raised to 150° C. and the corresponding pressure reached about 155 atm. The reaction was continued for 36 h. The catalyst was filtered off. The filtrate was concentrated and the residue was crystallised from EtOAc/isooctane to give 1.A (31.1 g, yield 50%).

mp: 135.9° C.; UV (EtOH): 211.4 nm (ε=90.9); IR (KBr): 3284, 1734, 1259, 1015 cm$^{-1}$; $^1$H-NMR (DMSO-d$_6$): δ 1.13 (3H,m); 2.06 (3H,m); 2.30 (1H,m); 3.47 (2H,m); 3.61 (3H, s); 4.70 (2H,d) ppm.

Similarly as described above, but replacing methyl 3,5-dihydroxybenzoate by:
Methyl 3,5-dihydroxy-4-methylbenzoate or
Methyl 3,5-dihydroxy-4-ethylbenzoate,
the following compounds were obtained:
Methyl all-cis-3,5-dihydroxy-4-methyl-cyclohexanecarboxylate: 1.B (R=Me, A=COOCH$_3$)
mp: 123° C.; $^1$H-NMR (500 MHz, CD$_3$OD): δ 3.698 (2H,dt,J=4.0,12.0 Hz); 3.666 (3H,s); 2.40 (2H,tt,J=4.0,13.0 Hz); 2.23 (1H,m); (2H,dt,J=4.0,13.0 Hz); 1.54 (2H,q,J=13.0 Hz); 0.88 (3H,d,J=7.08 Hz) ppm.
Methyl all-cis-4-ethyl-3,5-dihydroxy-cyclohexanecarboxylate: 1.C (R=Et, A=COOCH$_3$)
mp: 94–96° C.; $^1$H-NMR (500 MHz, MeOD): δ 3.72 (2H, dt, J=10.9, 4.1 Hz), 3.66 (3H, s), 2.42 (1H, m), 1.86 (1H, bs), 1.79 (2H, dt, J=12.8, 4.1 Hz), 1.59 (2H, d, J=9.0 Hz), 1.46 (2H, m), 1.02 (3H, t, J=7.5 Hz) ppm.

PREPARATION OF INTERMEDIATES OF FORMULA 2 AND 2' (scheme 1)

I) Enzymatic Esterification of Diols with General Formula (I)

Ia) Methyl (1S,3S,5R)-3-acetoxy-5-hydroxy-cyclohexanecarboxylate: 2.A (R=H, Z=Me, A=COOCH$_3$).

Methyl cis,cis-3,5-dihydroxy-cyclohexanecarboxylate 1.A (R=H, A=COOCH$_3$) (15.2 g, 87 mmol) and lipase from porcine pancreas (PPL –16.8 U/mg, 9.12 g) were placed in a round-bottom flask, followed by addition of vinylacetate (450 ml) at room-temperature. The flask was purged with nitrogen. The suspension was stirred in dark for 22 h, then filtered through a pad of celite to remove the lipase. The filtrate was concentrated by evaporation. The residue was separated by filtration through a pad of silica gel (70–200 Mesh, 45 g). Elution with toluene (210 ml) followed with a mixture of toluene/ethyl acetate 75/25 (V/V, 210 ml) then 50/50 (V/V, 210 ml) and finally ethyl acetate (240 ml) afforded after concentration 2.A (R=H, Z=Me, A=COOCH$_3$) (22.3 g, quantitative yield) as a yellow oil.

IR (film): 3447, 1734, 1243 cm$^{-1}$; $^1$H-NMR (CDCl$_3$): δ 1.4 (3H,m), 2.1 (3H,s), 2.3 (5H,m), 3.7 (3H,s), 3.75 (1H,m), 4.7 (1H,m) ppm; [α]$_D^{25}$: +22.4 (c=1.25, CHCl$_3$).

Ib) Methyl (1R,3S,4S,5R)-5-acetoxy-3-hydroxy-4-methyl cyclohexane carboxylate: 2'.B (R=Me, Z=Me, A=COOCH$_3$) and Methyl (1R,3S,4S,5R)-5-acetoxy-3-hydroxy-4-ethyl cyclohexanecarboxylate: 2'.C (R=Et, Z=Me, A=COOCH$_3$)

By a similar process as described under I.a, but replacing PPL by SAM II, PSL or CCL from respectively:

Methyl all cis-3,5-dihydroxy-4-methyl-cyclohexanecarboxylate: 1.B (R=Me, A=COOCH$_3$)

Methyl all cis dihydroxy-4-ethyl-3,5-cyclohexanecarboxylate: 1.C (R=Et, A=COOCH$_3$), the following compounds were obtained:

Methyl (1R,3S,4S,5R)-5-acetoxy-3-hydroxv-4-methyl-cyclohexane-carboxlate: 2'.B
(R=Me, Z=Me, A=COOCH$_3$):

IR (film): 3434, 1731, 1439, 1243, 1027 cm$^{-1}$; $^1$H-NMR (500 MHz, CDCl$_3$): δ 4.84 (1H, dt, J=4.3, 4.3 Hz); 3.82 (1H,m); 3.69 (3H,s); 2.45 (1H,m); 2.32 (1H,d, J=6.4 Hz); 2.05 (3H,s); 1.92 (2H,dt, J=4.0, 4.0 Hz); 1.77 (3H,m); 0.96 (3H,d, J=7.0 Hz) ppm; MS (m/z): 231 (M+, 1); 213; 199; 186; 170; 152; 127; 111; 83; 87; 67; 43 (base peak); $[\alpha]_D^{25}$: −22.7 (c=0.38, CHCl$_3$).

Methyl (1R,3S,4S,5R)-5-acetoxy-4-ethyl-3-hydroxy-cyclohexane-carboxylate: 2'.C (R=Et, Z=Me, A=COOCH$_3$):

IR (film): 3421, 2958, 2360, 1733, 1437, 1239, 1027, 739 cm$^{-1}$; $^1$H-NMR (500 MHz, CDCl$_3$): δ 4.98 (1H, t, J=4.1 Hz), 3.87 (1H, m), 3.69 (3H, s), 2.60 (1H, bs), 2.16 (2H, m), 2.02 (3H, s), 1.84 (2H, m), 1.72 (1H, bs), 1.59 (2H, m), 1.47 (1H, m), 0.97 (3H, t, J=7.5 Hz) ppm; MS (m/z): 245 (M$^+$+1), 233, 206, 184, 166, 141, 125, 111, 95, 87, 57, 43 (base peak). $[\alpha]_D^{25}$: −50.2 (c=1.08, CHCl$_3$).

II) Enzymatic Saponilication of di-esters of Formula 3

IIa) Methyl (1S,3S,5R)-3-acetoxy-5-hydroxy-cyclohexane-carboxylate: 2.A (R=H, Z=Me, A=COOCH$_3$).

To a solution of meso-diacetate 3.A (R=H, Z=Me, A=COOCH$_3$) (92.1 mg, 0.36 mmol) in 3.0 ml of CH$_3$CN was added 27.0 ml of buffer pH=7.0, followed by the addition of SAM II (13.8 mg, 46.8 U/mg). The resulting mixture was stirred at room temperature and the pH was maintained at 7.0 by the measured addition of a 1.0 M NaOH solution. The reaction was monitored by TLC analyses. The reaction was terminated by the addition of NaCl to saturate the reaction solution. The reaction mixture was extracted with AcOEt (3×50 ml). The combined organic extracts were washed with brine (3×10 ml), dried with MgSO$_4$ and concentrated. The residue was purified by HPLC eluting with isooctane/EtOAc (6:4) to give monoacetate 2.A (R=H, Z=Me, A=COOCH$_3$) (30.1 mg, 38.9%) as a colorless oil.

IIb) Methyl (1S,3R,4R,5S)-3-butanoyloxy-5-hydroxy-4-methyl-cyclohexane-carboxylate: 2B (R=Me, Z=n-C$_3$H$_7$, A=COOCH$_3$).

To a solution of 1.B (R=Me, A=COOCH$_3$) (0.2 g, 1.10 mmol) in 2 ml of CH$_2$Cl$_2$ was added butyric anhydride (538 μl, 3.29 mmol) at room temperature, followed by a solution of TMSoTf (trimethylsilyl triflate) (25 μl, 1M). The mixture was stirred at room temperature for 30 min. and then 2.5 ml of MeOH were added and the mixture was stirred for another 2 h, and quenched with 5% NaHCO$_3$. The reaction solution was washed with brine (3×20 ml), dried with MgSO$_4$ and concentrated to give a residue. The residue was purified by chromatography on silica gel cluting with isooctane: AcOEt (9:1) to give dibutyrate 3.B (R=Me, Z=n-C$_3$H$_7$, A=COOCH$_3$) (3.9 g, 98.8%) as a colorless oil. To a solution of this meso-diester (110 mg, 0.34 mmol) in 2.0 ml of CH$_3$CN was added 22.0 ml of buffer (pH=7.0), followed by the addition of SAM II (37 mg, 46.8 U/mg). The resulting mixture was stirred at room temperature and the pH was maintained at 7.0 by the measured addition of a 1.0 M NaOH solution. The reaction was monitored by TLC analyses. The reaction was terminated by the addition of NaCl to the reaction solution. The reaction mixture was extracted with EtOAc (3×50 ml), dried with MgSO$_4$ and concentrated to give a residue. The residue was purified by HPLC eluting with isooctane/EtOAc (7:3) to give monobutyrate 2.B (R=Me, Z=n-C$_3$H$_7$, A=COOCH$_3$) (78 mg, 90%) as a colorless oil.

IR (film): 3495, 2964, 2878, 1731, 1438, 1281, 1183, 990 cm$^{-1}$, $^1$H-NMR (CDCl$_3$): 4.83 (1H, dt), 3.83 (1H, m), 3.68 (3H, s), 2.45 (1H, m), 2.32 (1H, m), 2.28 (2H, t, J=7.9 Hz), 1.91 (2H, m), 1.82–1.62 (5H, m), 0.95 (6H, m). $[\alpha]_D^{25}$: +16.2 (c=2.09, CHCl$_3$); MS: 259 (M$^+$+1), 227, 214, 187, 170, 152, 127, 111, 93, 71, 43.

IIc) Methyl (1S,3R,4R,5S)-3-acetoxy-5-hydroxy-4-methyl-cyclohexane-carboxylate: 2.C (R=Me, Z=Me, A=COOCH$_3$)

From meso-diacetate 3.C (R=Me, Z=Me, A=COOCH$_3$) as described under IIa). $[\alpha]_D^{25}$: +20 (c=2.9, CHCl$_3$).

IId) Methyl (1R,3S,4S,5R)-5-acetoxy-3-hydroxy-4-methyl-cyclohexane-carboxylate: 2'.B (R=Me, Z=Me, A=COOCH$_3$)

From meso-diacetate 3.C (R=Me, Z=Me, A=COOCH$_3$) as described under IIa) but with PPL as lipasc.

$[\alpha]_D^{25}$: −19.5 (c=2.88, CHCl$_3$).

EXAMPLE 1

(2S, 3aS, 4aS)-2-t-butyldimethylsilyloxy-3a-carbomethoxy-bicyclo[3.1.0]hexane: I.b.1 (A=COOCH$_3$, R=H, P=TBDMS)

a) Methyl (1R,3S,5R)-3-acetoxy-5-tosyloxy-cyclohexanecarboxylate: 2.4.a (R=H, L=OTos, A=COOCH$_3$).

p-Toluenesulfonylchloride (13.3 g, 70 mmol) was added to a solution of methyl (1S,3S,5R)-3-acetoxy-5-hydroxy-cyclohexanecarboxylate 2.A (R=H, Z=Me, A=COOCH$_3$) (10.1 g, 43.7 mmol) and dimethylamino-pyridine (0.1 g) in a mixture of triethylamine (50 ml) and methylene chloride (10 ml) at 0° C. The solution was stirred for 1 h at 0° C. then 22 h at room temperature. The reaction was quenched with water (300 ml) and extracted with methylene chloride. The organic layer was washed with water, dried over MgSO$_4$, filtered and concentrated. The crude product was crystallized from EtOH affording 2.4.a (R=H, L=OTos, A=COOCH$_3$) (13.2 g, 81.6%).

mp: 83.1° C.; IR (KBr): 1734, 1175 cm$^{-1}$; $^1$H-NMR (CDCl$_3$): δ 1.5 (3H,m), 2.0 (3H,s), 2.28 (4H,m), 2.47 (3H,s), 3.68 (3H,s), 4.4 (1H,m), 4.68 (1H,m), 7.35 (1H,d, J=8.5 Hz), 7.8 (2H,d, J=8.5 Hz) ppm.

b) Methyl (1R,3S,5R)-3-hydroxy-5-tosyloxy-cyclohexanecarboxylate: 2.5.a (R=H, L=OTos, A=COOCH$_3$).

To a suspension of 2.4.a (R=H, L=OTos, A=COOCH$_3$) (23.35 g, 63 mmol) in MeOH, was added potassium carbonate (4.36 g, 31 mmol). The suspension was stirred for 30 min. and poured in water (1.5 L). The precipitate was filtered and dried to give 2.5.a (R=H, L=OTos, A=COOCH$_3$) (18.5 g, 89%).

mp: 98.4° C.; UV (EtOH): 225 nm (ε=11935); IR (KBr): 3447, 1719, 1176 cm$^{-1}$; $^1$H-NMR (CDCl$_3$): δ 1.52 (4H,m), 2.25 (4H,m), 2.45 (3H,s), 3.6 (1H,m), 3.68 (3H,s), 4.42 (1H,m), 7.35 (2H,d, J=8.5 Hz), 7.8 (2H,d, J=8.5 Hz) ppm; $[\alpha]_D^{25}$: −19 (C=1.00, EtOH).

c) Methyl (1R,3R,5R)-3-benzoyloxy-5-tosyloxy-cyclohexanecarboxylate: 2.6.a (R=H, L=OTos, A=COOCH$_3$).

To a solution of 2.5.a (R=H, L=OTos, A=COOCH$_3$) (18.35 g, 56 mmol), triphenyl phosphine (18.4 g, 70 mmol) and benzoic acid (8.53 g, 70 mmol) in toluene (180 ml) and THF (70 ml) at 0° C. was added diethylazodicarboxylate (11 ml, 70 mmol). The mixture was stirred at room temperature for 30 min, after adding heptane (735 ml) it was filtered and the filtrate was concentrated. Toluene was added to the crude product and the solution was filtered through a pad of silica gel (30–70 Mesh). Elution with toluene then with a mixture of toluene/methylene chloride afforded after concentration a residue which was crystallized from EtOH to give 2.6.a (R=H, L=OTos, A=COOCH$_3$) (19.77 g, 82%).

mp: 76.2° C.; UV (EtOH): 227 nm ($\epsilon$=20840); IR (KBr): 1709, 1177 cm$^{-1}$; $^1$H-NMR (CDCl$_3$): $\delta$ 1.7 (3H,m), 2.14 (2H,m), 2.35 (3H,s), 2.48 (1H,m), 2.83 (1H,m), 3.18 (3H,s), 4.75 (1H,m), 5.43 (1H,m), 7.2 (2H,d, J=11.4 Hz), 7.5 (2H,d, J=8.5 Hz), 7.6 (1H,m), 7.75 (2H,d, J=11.4 Hz), 7.94 (2H,d, J=8.5 Hz) ppm; $[\alpha]_D^{25}$: −65.8 (c=0.98, EtOH).

d) Methyl (1R,3R,5R)-3-hydroxy-5-tosyloxy-cyclohexanecarboxylate: 2.7.a (R=H, L=OTos, A=COOCH$_3$).

To a suspension of 2.6.a (R=H, L=OTos, A=COOCH$_3$) (19.77 g, 46 mmol) in MeOH (260 ml), was added potassium carbonate (3.16 g, 22.9 mmol). The mixture was stirred for 6 h at room temperature and poured into water (1 L). The aqueous layer was extracted with diisopropyloxide, dried over MgSO$_4$, filtered and concentrated affording 2.7.a (R=H, L=OTos, A=COOCH$_3$) (17.45 g, quant.) as an oil.

UV (EtOH): 224 nm ($\epsilon$=12262); IR (KBr): 3525, 1731, 1174 cm$^{-1}$; $^1$H-NMR (CDCl$_3$): $\delta$ 1.67 (3H,m), 2.1 (3H,m), 2.45 (3H,s), 2.85 (1H,m), 3.7 (3H,s), 4.3 (1H,s), 4.82 (1H,m), 7.35 (2H,d, J=8.5 Hz), 7.8 (2H,d, J=8.5 Hz) ppm; $[\alpha]_D^{25}$: −36.7 (c=1.06, CHCl$_3$).

e) Methyl (1,R,3R,5R)-3-t-butyldimethylsilyloxy-5-tosyloxy-cyclohexane-carboxylate: 2.8.a (R=H, L=OTos, P=TBDMS, A=COOCH$_3$).

To a solution of 2.7.a (R=H, L=OTos, A=COOCH$_3$) (17.45 g, 46 mmol) and imidazole (3.9 g, 57 mmol) in dry dimethylformamide (80 ml) was added t-butyldimethylsilyl chloride (8.6 g, 57 mmol). The mixture was stirred at room temperature for 1.5 h, then poured on water and extracted with toluene. The organic layer was washed with water then concentrated. The crude product was crystallized from heptane to afford 2.8.a (R=H, L=OTos, P=TBDMS, A=COOCH$_3$) (13.94 g, 69%).

mp: 68.2° C.; UV (EtOH): 225 nm ($\epsilon$=12390); IR (KBr): 2853, 1726, 1436, 1359, 1173, 831 cm$^{-1}$; $^1$H-NMR (CDCl$_3$): $\delta$ 0.02 (3H,s), 0.05 (3H,s), 0.82 (9H,s), 1.55 (4H,m), 1.85 (2H,m), 2.45 (3H,s), 2.8 (1H,m), 3.67 (3H,s), 4.2 (1H,bs), 4.7 (1H,m), 7.33 (2H, d, J=8.5 Hz), 7.8 (2H,d, J=8.5 Hz) ppm; $[\alpha]_D^{25}$: −41.6 (c=1.00, EtOH).

f) (2S,3aS,4aS)-2-t-butyldimethylsilyloxy-3a-carbomethoxy-bicyclo[3.1.0]hexane: I.b.1 (R=H, P=TBDMS, A=COOCH$_3$).

To a stirred solution of 2.8.a (R=H, L=OTos, P=TBDMS, A=COOCH$_3$) (378.5 g, 856 mmol) in t-butanol at 64° C. was added slowly during 1 h a 1M solution of potassium t-butylate in t-butanol (1.02 L). 5 Minutes after the end of the addition the suspension was cooled to 30° C. and a saturated solution of ammonium chloride (3 L) was added. After 10 min. the aqueous phase was extracted with diisopropyloxide. The organic layer was washed with water, dried over MgSO$_4$, filtered and concentrated. The residue was flash-chromatographed on silica gel with a mixture of heptane/ethyl acetate as eluting solvent giving I.b.1 (R=H, P=TBDMS, A=COOCH$_3$) (211.3 g, 91.3%) as a yellow oil. Eb$_{760}$: 135° C.; UV (EtOH): 201 nm ($\epsilon$=742); IR (film) 1726 cm$^{-1}$, 1458 cm$^{-1}$, 1437 cm$^{-1}$, 1254 cm$^{-1}$, 837 cm$^{-1}$; $^1$H-NMR (CDCl$_3$): $\delta$ 0.01 (6H,s), 0.83 (9H,s), 1.28 (2H,m), 1.8 (2H,m), 2.11 (3H,m), 3.65 (3H,s), 3.9 (1H,m) ppm; $[\alpha]_D^{25}$: −43 (c=1.04, EtOH).

EXAMPLE 2

(2S,3aS,4aS)-2-t-butyldimethylsilyloxy-3a-(hydroxymethyl)-bicyclo[3.1.0]hexane: I.b.2 (R=H, P=TBDMS, A=CH$_2$OH)

To a solution of (2S,3aS,4aS)-2-t-butyldimethylsilyloxy-3a-carbomethoxy-bicyclo[3.1.0]hexane I.b.1 (R=H, P=TBDMS, A=COOCH$_3$) (207.5 g, 768 mmol) in toluene (2.1 L) at −70° C. was added a 1.5 M solution of diisobutylaluminium hydride in toluene (1.25 L) over 1.5 h. After completion of the addition, a saturated solution of potassium sodium tartrate was slowly added and the temperature was raised to 0° C. After stirring for 2 h the reaction mixture was extracted with toluene, the organic layer was dried over MgSO$_4$ and concentrated to give 142.9 g (88%) of the title compound I.b.2 as a yellow oil.

IR (KBr): 3355, 1471, 1255, 835, 774 cm$^{-1}$; $^1$H-NMR (CDCl$_3$): $\delta$ 0 (6H,s), 0.32 (1H,m), 0.5 (1H,m), 0.83 (9H,s), 1.16 (1H,m), 1.87 (5H,m), 3.54 (2H,m), 4.0 (1H,m) ppm.

EXAMPLE 3

(2S,3aS,4aS) -2-t-butyldimethylsilyloxy-3a-formyl-bicyclo[3.1.0]hexane: I.b.3 (R=H, P=TBDMS, A=CHO)

To I.b.2 (R=H, P=TBDMS, A=CH$_2$OH) (69.6 g, 287 mmol) in methylene chloride (700 ml) at room temperature was added pyridinium chlorochromate (68 g, 315 mmol). The mixture was stirred vigorously for 1 h. The temperature went up to 35° C. then decreased to 25° C. The suspension was filtered through a pad of celite and washed with methylene chloride and diisopropyloxide. The organic layer was washed succesively with water, a saturated solution of sodium hydrogencarbonate and with water to pH 6–7. The combined organic layers were dried over MgSO$_4$, filtered and concentrated. The residue (66.8 g) was purified by flash-chromatography on florisil with heptane/ethyl acetate 95/5 (V/V) as eluent to give I.b.3 (R=H, P=TBDMS, A=CHO) as a yellow oil (50.33 g, 73%).

UV (EtOH): 204 nm ($\epsilon$=6292); IR (KBr): 1726, 1253, 1119, 838 cm$^{-1}$; $^1$H-NMR (CDCl$_3$): $\delta$ 0 (6H,s), 0.87 (9H,s), 1.3 (2H,m), 1.85 (2H,m), 2.1 (3H,m) 4 (1H,m), 8.9 (1H,s) ppm; $[\alpha]_D^{25}$: −49.4 (c=1.06, EtOH).

EXAMPLE 4

(2R,3aR,4aR)2-t-Butyldimethylsilyloxy-3a-carbomethoxy-bicyclo[3.1.0]hexane: I.h.1 (R=H, A=COOCH$_3$, P=TBDMS)

a) Methyl (1R,3S,5S)-3-acetoxy-5-benzoyloxy-cyclohexanecarboxylate: 3.9.a R=H, A=COOCH$_3$).

As described for 2.6.a (R=H, L=OTos, A=COOCH$_3$), methyl (1S,3S,5R)-3-acetoxy-5-hydroxy-cyclohexanecarboxylate 2.A (R=H, Z=Me, A=COOCH$_3$) (25 g, 111.3 mmol) was converted to methyl (1R,3S,5S) 3-acetoxy-5-benzoyloxy-cyclohexanecarboxylate 3.9.a (R=H, A=COOCH$_3$) (32.4 g, 91%).

$^1$H-NMR (CDCl$_3$): $\delta$ 1.68 (3H,m), 2.05 (3H,s), 2.34 (3H,m), 2.92 (1H,m), 3.70 (3H,s), 5.18 (1H,m), 5.55 (1H, m), 7.50 (3H,m), 8.05 (2H,m) ppm; $[\alpha]_D^{25}$: +42.3 (c=0.82, CHCl$_3$).

b) Methyl (1R,3S,5S)-5-benzoyloxy-3-hydroxy-cyclohexanecarboxylate: 3.10.a (R=H, A=COOCH$_3$).

Methyl (1R,3S,5S)-3-acetoxy-5-benzoyloxy-cyclohexanecarboxylate 3.9.a (R=H, A=COOCH$_3$) (32.4 g, 151.9 mmol) was saponified as described for 2.5.a (R=H, L=OTos, A=COOCH$_3$). The crude product was purified by flash chromatography on silica gel (heptane/ethyl acetate 5/5) to give 3.10.a (R=H, A=COOCH$_3$) (22.38 g, 79.5%).

$^1$H-NMR (CDCl$_3$): δ 1.63 (4H,m), 1.92 (1H,s), 2.3 (2H, m), 2.86 (1H,m), 3.7 (3H,s), 4.1 (1H,m), 5.53 (1H,m), 7.5 (3H,m), 8.0 (2H,m) ppm; $[\alpha]_D^{25}$: −13.5 (c=1.43, CHCl$_3$).

c) Methyl (1S,3S,5S)-5-benzoyloxy-3-tosyloxy-cyclohexanecarboxylate: 3.11.a (R=H, L=OTos, A=COOCH$_3$).

Alcohol 3.10.a (R=H, A=COOCH$_3$) (25.2 g, 90.88 mmol) was tosylated as described for 2.4.a (R=H, L=OTos, A=COOCH$_3$). After purification by flash chromatography (heptane/ethyl acetate 7/3) and crystallization from heptane/EtOH, title compound 3.11.a (R=H, L=OTos, A=COOCH$_3$) (39.75 g) was obtained in quantitative yield.

mp: 128.4° C.; IR (KBr): 2950, 1715, 1175, 939 cm$^{-1}$; $^1$H-NMR (CDCl$_3$): δ 1.7 (3H,m), 2.18 (2H,m), 2.38 (3H,s), 2.5 (1H,m), 2.85 (1H,m), 3.68 (3H,s), 4.76 (1H,m), 5.43 (1H,m), 7.19 (2H,d), 7.5 (2H,d), 7.58 (1H,m), 7.77 (2H,d), 7.96 (2H,d) ppm; $[\alpha]_D^{25}$: +69 (c=1.014, CHCl$_3$).

d) Methyl (1S,3S,5S)-5-hydroxy-3-tosyloxy-cyclohexanecarboxylate: 3.12.a (R=H, L=OTos, A=COOCH$_3$).

From 3.11.a (R=H, L=OTos, A=COOCH$_3$) (38.25 g, 88.4 mmol). as described for 2.7.a (R=H, L=OTos, A=COOCH$_3$), methyl (1S,3S,5S)-5-hydroxy-3-tosyloxy-cyclohexanecarboxylate 3.12.a (R=H, L=OTos, A=COOCH$_3$) (29.25 g) was obtained in quantitative yield as a yellow oil.

$^1$H-NMR (CDCl$_3$): δ 1.6 (4H,m), 2.08 (3H,m), 2.47 (3H,s), 2.83 (1H,m), 3.68 (3H,s), 4.3 (1H,m), 4.82 (1H,m), 7.36 (2H,d), 7.8 (2H,d) ppm.

e) Methyl (1S,3S,5S)-5-t-butyldimethylsilyloxy-3-tosyloxy-cyclohexane-carboxylate: 3.13.a (R=H, L=OTos, P=TBDMS, A=COOCH$_3$).

From 3.12.a (R=H, L=OTos, A=COOCH$_3$) (29.2 g, 89.07 mmol) as described for 2.8.a (R=H, L=OTos, P=TBDMS, A=COOCH$_3$). Purification by flash chromatography on silica gel (heptane/ethyl acetate 8/2) gave 3.13.a (R=H, L=OTos, P=TBDMS, A=COOCH$_3$) (34.8 g, 88%) as a yellow oil.

IR (film): 2953, 2855, 1725, 1278, 1177, 949 cm$^{-1}$; $^1$H-NMR (CDCl$_3$): δ 0 (6H,d), 0.85 (9H,s), 1.55 (3H,m), 1.88 (2H,m), 2.38 (1H,s), 2.48 (3H,s), 2.82 (1H,m), 3.7 (3H, s), 4.2 (1H, m), 4.7 (1H,m), 7.8 (2H, d), 8.09 (2H,d) ppm; $[\alpha]_D^{25}$: +29.5 (c=1.06, EtOH).

f) (2R,3aR,4aR)-2-t-butyldimethylsilyloxy-3a-carbomethoxy-bicyclo[3.1.0]hexane: I.h.1 (R=H, P=TBDMS, A=COOCH$_3$).

From 3.13.a (R=H, L=OTos, P=TBDMS, A=COOCH$_3$) (33.2 g, 75 mmol) as described for I.b.1 (from 2.8.1). Purification by flash chromatography on silica gel (heptane/ethyl acetate 95/5) afforded (2R,3aR,4aR)-2-t-butyldimethylsilyloxy-3a-carbomethoxy-bicyclo[3.1.0] hexane I.h.1 (R=H, P=TBDMS, A=COOCH$_3$) (15.5 g, 78%) as a yellow oil.

IR (film): 2952, 2856, 1724, 1113, 837 cm$^{-1}$; $^1$H-NMR (CDCl$_3$): δ 0 (6H,s), 0.85 (9H,s), 1.11 (1H,d), 1.27 (2H,m), 1.6 (3H,s), 1.8 (1H,m), 2.11 (3H,m), 3.65 (3H, s), 3.9 (1H, m) ppm; $[\alpha]_D^{25}$: +38.3 (c=1.122, EtOH).

EXAMPLE 5

(2R,3aR,4aR)-2-t-butyldimethylsilyloxy-3a-(hydroxymethyl)-bicyclo[3.1.0]hexane: I.h.2 (R=H, P=TBDMS, A=CH$_2$OH)

(2R,3aR,4aR)-2-t-butyldimethylsilyloxy-3a-carbomethoxy-bicyclo[3.1.0]hexane I.h.1 (R=H, P=TBDMS, A=COOCH$_3$) (15.15 g, 56 mmol) was converted to I.h.2 (R=H, P=TBDMS, A=CH$_2$OH) (11.85 g, 87%) using the conditions described for I.b.2 (R=H, P=TBDMS, A=CH$_2$OH).

IR (film): 3354, 2928, 2856, 1255, 835 cm$^{-1}$; $^1$H-NMR (CDCl$_3$): δ 0.1 (6H,s), 0.35 (1H,t), 0.5 (1H,t), 0.86 (9H,s), 1.17 (1H,s), 1.85 (5H,m), 3.52 (2H,m), 4.0 (1H, m) ppm; $[\alpha]_D^{25}$: +17.4 (c=1.15, EtOH).

EXAMPLE 6

(2R,3aR,4aR)-2-t-butyldimethylsilyloxy-3a-formyl-bicyclo[3.1.0]hexane: I.h.3 (R=H, P=TBDMS, A=CHO)

From I.h.2 (R=H, P=TBDMS, A=CH$_2$OH) (11.3 g, 46.6 mmol), following the procedure of I.b.3 (R=H, P=TBDMS, A=CHO) I.h.3 (R=H, P=TBDMS, A=CHO) was obtained (6.2 g, 55%) as a yellow oil.

UV (EtOH): 204.5 mm (ε=6600); IR (film): 2930, 2880, 2856, 1705, 1119, 1097, 836 cm$^{-1}$; $^1$H-NMR (CDCl$_3$): δ 0 (6H,s), 0.83 (9H,s), 0.95 (1H,t), 1.22 (2H,m), 1.85 (2H,m), 2.1 (3H,m), 4.0 (1H,quintuplet), 8.87 (1H, s) ppm; $[\alpha]_D^{25}$: +53.6 (c=1.008, EtOH).

EXAMPLE 7

(2R,3aS,4aS)-2-t-butyidimethylsilyloxy-3a-carbomethoxy-bicyclo[3.1.0]hexane: I.a.1 (R=H, P=TBDMS, A=COOCH$_3$)

a) Methyl (1R,3S,5R)-3-t-butyldimethylsilyloxy-5-tosyloxy-cyclohexane-carboxylate: 2.3.a (R=H, L=OTos, P=TBDMS, A=COOCH$_3$).

The hydroxy function of methyl (1R,3S,5R)-3-hydroxy-5-tosyloxy-cyclohexanecarboxylate 2.5.a (R=H, L=OTos, A=COOCH$_3$) (29.3 g, 89.2 mmol) was protected as described for 2.8.a (R=H, L=OTos, P=TBDMS, A=COOCH$_3$) to yield 2.3.a (R=H, L=OTos, P=TBDMS, A=COOCH$_3$), (36,75 g, 93%).

mp: 70.9° C.; IR (KBr): 2957, 2855, 1734, 1174, 923 cm$^{-1}$; $^1$H-NMR (CDCl$_3$): δ 0 (6H,s), 0.82 (3H,s), 1.41 (3H,m), 2.16 (4H,m), 2.46 (3H,s), 3.54 (1H,m), 3.69 (3H,s), 4.41 (1H,m), 7.34 (2H,d), 7.8 (2H,d) ppm; $[\alpha]_D^{25}$: −8.2 (c=1.2, EtOH).

b) (2R,3aS,4aS)-2-t-butyldimethylsilyloxy-3a-carbomethoxy-bicyclol3.1.0lhexane: I.a.1 (R=H, P=TBDMS, A=COOCH$_3$).

From 2.3.a (R=H, L=OTos, P=TBDMS, A=COOCH$_3$) (34.81 g, 78.6 mmol) as described for I.b.1 (R=H, P=TBDMS, A=COOCH$_3$). Purification by flash chromatography on silica gel (heptane/ethyl acetate 5/5) gave I.a.1 (R=H, P=TBDMS, A=COOCH$_3$) (16.6 g, 78%) as a yellow oil.

IR (film): 2953, 2855, 1726, 1148, 836 cm$^{-1}$; $^1$H-NMR (CDCl$_3$): δ 0 (6H,s), 0.86 (9H,s), 1.5 (5H,m), 2.1 (1H,m), 2.48 (1H,m), 3.68 (3H,s), 4.33 (1H,t) ppm; $[\alpha]_D^{25}$: −60.1 (c=0.998, EtOH).

EXAMPLE 8

(2R,3aS,4aS)-2-t-butyldimethylsilyloxy-3a-(hydroxymethyl)-bicyclo[3.1.0]hexane: I.a.2 (R=H, P=TBDMS, A=CH$_2$OH)

From I.a.1 (R=H, P=TBDMS, A=CH$_2$OH) (15.6 g, 57.7 mmol) as described for I.b.2 (R=H, P=TBDMS, A=CH$_2$OH). I.a.2 (R=H, P=TBDMS, A=CH$_2$OH) was obtained as a yellow oil (11.7 g, 83.7%).

IR (film): 3331, 2927, 2855, 1254, 1094, 1006, 835 cm$^{-1}$; $^1$H-NMR (CDCl$_3$): δ 0 (6H,s), 0.5 (1H,m), 0.88 (9H,s), 1.19 (3H,m), 1.72 (2H,m), 2.1 (2H,m), 3.6 (2H,s), 4.34 (1H,t) ppm; $[\alpha]_D^{25}$: −23.5 (c=1.062, EtOH).

EXAMPLE 9

(2R,3aS,4aS)-2-t-butyldimethylsilyloxy-3a-formyl-bicyclo[3.1.0]hexane: I.a.3 (R=H, P=TBDMS, CHO)

From I.a.2 (R=H, P=TBDMS, A=CH$_2$OH) (11.1 g, 45.5 mmol), as described for I.b.3 (R=H, P=TBDMS, A=CHO), I.a.3 (R=H, P=TBDMS, A=CHO) (8.8 g, 80%) was obtained as a yellow oil.

UV (EtOH): 204.7 nm (ε=6991); IR (film): 2928, 2855, 1702, 1255, 1072, 837 cm$^{-1}$; $^1$H-NMR (CDCl$_3$): δ 0 (6H,s), 0.85 (9H,s), 1.45 (1H,m), 1.78 (3H,m), 2.02 (2H,m), 2.5 (1H,m), 4.35 (1H,m), 8.81 (1H,s) ppm; $[\alpha]_D^{25}$: −71.8 (c=1.406, EtOH).

EXAMPLE 10

(2S,3aR,4aR)-2-t-butyldimethylsilyloxy-3a-carbomethoxy-bicyclo[3.1.0]hexane: I.f.1 (R=H, P=TBDMS, A=COOCH$_3$)

a) Methyl (1R,3S,5R)-3-acetoxy-5-t-butyldimethylsilyloxy-cyclohexane-carboxylate: 3.7.a (R=H, P=TBDMS, A=COOCH$_3$).

The hydroxy function of methyl (1S,3S,5R)-3-acetoxy-5-hydroxycyclohexanecarboxylate 2.A (R=H, A=COOCH$_3$) (45.5 g, 0.210 mmol) was silylated as described for 2.8.a (R=H, L=OTos, P=TBDMS, A=COOCH$_3$). Purification by flash chromatography on silica gel with a mixture of heptane/ethyl acetate as eluting solvent (9/1) gave 3.7.a (R=H, P=TBDMS, A=COOCH$_3$) as a yellow oil (69.97 g, 92%).

IR (film): 2953, 2856, 1736, 1240 cm$^{-1}$; $^1$H-NMR (CDCl$_3$): δ 0 (6H,s), 0.8 (9H,s), 1.33 (4H,m), 2 (3H,s), 2.1 (2H,m), 2.32 (1H,m), 3.55 (1H,m), 3.62 (3H,s), 4.66 (1H,m) ppm.

b) Methyl (1R,3S,5R)-5-t-butyldimethylsilyloxy-3-hydroxy-cyclohexane-carboxylate: 3.8.a (R=H, P=TBDMS, A=COOCH$_3$).

From 3.7.a (R=H, P=TBDMS, A=COOCH$_3$) (63.67 g, 0.1926 mmol) as described for 2.5.a (R=H, L=OTos, A=COOCH$_3$). Purification by flash chromatography on silica gel with heptane/ethyl acetate (7/3) as eluent gave 3.8.a (R=H, P=TBDMS, A=COOCH$_3$) (46,24 g, 83%) as a yellow oil.

IR (film): 3404, 2952, 2856, 1736, 837 cm$^{-1}$; $^1$H-NMR (CDCl$_3$): δ 0 (6H,s), 0.81 (9H,s), 1.3 (3H,m), 1.67 (1H,m), 2.13 (4H,m), 3.56 (2H,m), 3.63 (3H,s) ppm; $[\alpha]_D^{25}$: +6.8 (c=1.036, CHCl$_3$).

c) Methyl (1S,3S,5R)-5-t-butyldimethylsilyloxy-3-tosyloxy-cyclohexane-carboxylate: 3.6.a (R=H, L=OTos, P=TBDMS, A=COOCH$_3$).

From 3.8.a (R=H, P=TBDMS, A=COOC'H$_3$) (45.99 g, 0.159 mmol) as described for 2.4.a (R=H, L=OTos, A=COOCH$_3$). Purification by flash chromatography on silica gel with heptane/ethyl acetate 8/2 as eluent followed by crystallization from EtOH afforded 3.6.a (R=H, L=OTos, P=TBDMS, A=COOCH$_3$) (53.7 g, 76%).

mp: 71° C.; IR (KBr): 2957, 2855, 1734, 1174, 923 cm$^{-1}$; $^1$H-NMR (CDCl$_3$): δ 0 (6H,s), 0.82 (9H,s), 1.41 (3H,m), 2.16 (4H,m), 2.46 (3H,s), 3.54 (1H,m), 3.69 (3H,s), 4.41 (1H,m), 7.34 (2H,d), 7.8 (2H,d) ppm; $[\alpha]_D^{25}$: +6.8 (c=1.032, EtOH).

d) (2S,3aR,4aR)-2-t-butyldimethylsilyloxy-3a-carbomethoxy-bicyclo[3.1.0]hexane: I.f.1 (R=H, P=TBDMS, A=COOCH$_3$).

From 3.6.a (R=H, L=OTos, P=TBDMS, A=COOCH$_3$) (53.7 g, 0.121 mmol) as described for I.b.1 (R=H, P=TBDMS, A=COOCH$_3$). I.f.1 (R=H, P=TBDMS, A=COOCH$_3$) was obtained (24.48 g, 74.6%) as a pale yellow oil.

IR (film): 2953, 2856, 1726, 1148, 836 cm$^{-1}$; $^1$H-NMR (CDCl$_3$): δ 0 (6H,s), 0.86 (9H,s), 1.5 (5H,m), 2.1 (1H,m), 2.48 (1H,m), 3.68 (3H,s), 4.33 (1H,t) ppm; $[\alpha]_D^{25}$: +62.9 (c 1.066, EtOH).

EXAMPLE 11

(2S,3aR,4aR)-2-t-butyldimethylsilyloxy-3a-hydroxymethyl)-bicyclo[3.1.0]hexane: I.f.2 (R=H, P=TBDMS, A=CH$_2$OH)

From I.f.1 (R=H, P=TBDMS, A=COOCH$_3$) (10 g, 0.037 mmol) as described for I.b.2 (R=H, P=TBDMS, A=CH$_2$OH). I.f.2 (R=H, P=TBDMS, A=CH$_2$OH) was obtained in quantitative yield (10 g) as an oil.

IR (film): 3331, 2927, 2855, 1254, 1094, 1006, 835 cm$^{-1}$; $^1$H-NMR (CDCl$_3$): δ 0 (6H,s), 0.5 (1H,m), 0.88 (9H,s), 1.19 (3H,m), 1.72 (2H,m), 2.1 (2H,m), 3.6 (2H,s), 4.34 (1H,t) ppm; $[\alpha]_D^{25}$: +23.2 (c=0.99, EtOH).

EXAMPLE 12

(2S,3aR,4aR)-2-t-Butyldimethylsilyloxy-3a-formyl-bicyclo[3.1.0]hexane: I.f.3 (R=H, P=TBDMS, A=CHO)

As for I.b.3 (R=H, P=TBDMS, A=CHO), I.f.2 (R=H, P=TBDMS, A=CH$_2$OH) (10 g, 0.037 mmol) was transformed into I.f.3 (R=H, P=TBDMS, A=CHO) obtained as a pale yellow oil (5.3 g, 59.7%).

IR (film): 2928, 2855, 1702, 1255, 1072, 837 cm$^{-1}$; $^1$H-NMR (CDCl$_3$): δ 0 (6H,s), 0.85 (9H,s), 1.45 (1H,m), 1.78 (3H,m), 2.02 (2H,m), 2.5 (1H,m), 4.35 (1H,m), 8.81 (1H,s) ppm; UV (EtOH): 205 nm; $[\alpha]_D^{25}$: +70.4 (c=1.1, EtOH).

EXAMPLE 13

(2S,3aS,4aS)-2-t-butylidiphenylsilyloxy-3a-carbomethoxy-bicyclo[3.1.0]hexane: I.b.4 (R=H, P=TBDPS, A=COOCH$_3$)

a) Methyl (1R, 3S, 5R)-3-aetoxy-5-(4-bromobenzenesulfonyloxy)-cyclohexanecarboxylate: 2.4.b (R=H, L,=OBros, A=COOCH$_3$).

From 2.A (R=H) (1.4 g, 6.47 mmol) and 4-bromobenzenesulfonyl chloride (4.22 g, 16.19 mmol) as described for 2.4.a (R=H, L=OTos). 2.4.b (R=H, L=OBros, A=COOCH$_3$) (2.6 g, 96%) was obtained as white crystals.

mp: 110–111° C.; IR (film): 2956, 1734, 1363, 1246, 1188, 822, 742 cm$^{-1}$; $^1$H-NMR (500 MHz, CDCl$_3$): δ 7.76 (2H, d, J=8.6 Hz), 7.70 (2H, d, J=8.6 Hz), 4.68 (1H, dddd, J=11.6, 11.6, 4.37, 4.37 Hz), 4.46 (1H, dddd, 11.6, 11.6, 4.6, 4.6 Hz), 3.69 (3H, s), 2.37 (1H, m), 2.28 (2H, m), 2.02 (3H, s), 1.58 (2H, m), 1.39 (1H, dd, J=24.0, 12.4 Hz) ppm; MS (m/z): 419 (M$^+$, 1), 405 (1), 363 (3), 221 (10), 157 (34), 138 (70), 107 (15), 79 (68); $[\alpha]_D^{25}$: −10.65 (c=1.50, CHCl$_3$).

b) Methyl (1R, 3S, 5R)-5-(4-bromobenzenesulfonyloxy)-3-hydroxy-cyclohexanecarboxylate: 2.5.b (R=H, L=OBros, A=COOCH$_3$).

From 2.4.b (R=H, L=OBros, A=COOCH$_3$) (2.55 g, 6.08 mmol) as described for 2.5.a (R=H, L=OTos). 2.5.b (R=H, L=OBros, A=COOCH$_3$) was obtained (2.25 g, 98%) as white crystals.

mp: 95–98° C.; IR (film): 3397, 2954, 1734, 1396, 1186, 815, 740 cm$^{-1}$; $^1$H-NMR (500 MHz, CDCl$_3$): δ 7.76 (2H, d, J=8.6 Hz), 7.70 (2H, d, J=8.6 Hz), 4.46 (1H, dddd, J=11.5, 11.5, 4.5, 4.5 Hz), 3.68 (3H, s), 3.64 (1H, m), 2.25 (4H, m), 1.60 (1H, dd, J=24.2, 12.5 Hz), 1.48 (1H, dd, J=23.0, 11.5 Hz), 1.35 (1H, dd, J=23.8, 12.5 Hz) ppm; MS (m/z): 377 (M$^+$, 1), 328 (3), 235 (10), 221 (13), 156 (85), 113 (100), 97 (52), 79 (53); [α]$_D^{25}$: −17.13 (c=1.48, CHCl$_3$).

c) Methyl (1R,3R,5R)-3-benzoyloxy-5-(4-bromobenzenesulfonyloxy)-cyclohexanecarboxylate: 2.6.b (R=H, L=OBros, A=COOCH$_3$).

From 2.5.b (R=H, L=OBros, A=COOCH$_3$) (1.15 g, 3.05 mmol) as described for 2.6.a (R=H, L=OTos, A=COOCH$_3$). The yield is 1.13 g (73%).

mp: 131–133° C.; IR (film): 3420, 2948, 1717, 1362, 1186, 817, 707 cm$^{-1}$; $^1$H-NMR (500 MHz, CDCl$_3$): δ 7.95 (2H, d, J=7.4 Hz), 7.72 (2H, d, J=8.5 Hz), 7.60 (1H, t, J=7.4 Hz), 7.58 (2H, d, J=8.5 Hz), 7.49 (2H, t, 7.7 Hz), 5.46 (1H, m), 4.81 (1H, dddd, J=11.3, 11.3, 4.4, 4.4 Hz), 2.85 (1H, dddd, J=12.5, 12.5, 3.7, 3.7 Hz), 2.47 (1H, m), 2.20 (2H, m), 1.73 (3H, m) ppm; MS (m/z): 497 (M$^+$,1), 391 (4), 377 (10), 260 (100), 237 (8), 221 (25); [α]$_D^{25}$: −59.32 (c=1.79, CHCl$_3$).

d) Methyl (1R,3R,5R)-5-(4-bromobenzenesulfonyloxy)-3-hydroxy-cyclohexanecarboxylate: 2.7.b (R=H, L=OBros, A=COOCH$_3$).

From 2.6.b (R=H, L=OBros, A=COOCH$_3$) (240 mg, 0.483 mmol) as described for 2.7.a (R=H, L=OTos, A=COOCH$_3$). The yield is 167 mg (88%).

mp: 107–108° C. IR (film): 3527, 2954, 1732, 1577, 1365, 1187, 940, 818 cm$^{-1}$; $^1$H-NMR (500 MHz, CDCl$_3$): δ 7.78 (21H, d, J=8.6 Hz), 7.70 (2H, d, J=8.6 Hz), 4.87 (1H, dddd, J=10.9, 10.9, 4.5, 4.5 Hz), 4.31 (1H, m), 3.69 (3H, s), 2.86 (1H, dddd, J=12.1, 12.1, 3.7, 3.7 Hz), 2.24 (1H, d, J=12.7 Hz), 2.04 (1H, d, J=11.7 Hz),1.94 (1H, d, J=14.0 Hz), 1.65 (3H, m) ppm; MS (m/z): 394 (M$^+$+1, 1), 295 (2), 221 (4), 157 (11), 97 (10); [α]$_D^{25}$: −38.75 (c=0.80, CHCl$_3$).

e) Methyl (1R,3R,5R)-5-(4-bromobenzenesulfonyloxy)-3-t-butyldiphenylsilyloxy-cyclohexane carboxylate: 2.8.b (R=H, L=OBros, P=TBDPS, A=COOCH$_3$).

From 2.7.b (R=H, L=OBros, A=COOCH$_3$) (299 mg, 0.760 mmol) as described for 2.8.a (R=H, L=OTos, P=TBDPS, A=COOCH$_3$). 2.8.b (R=H, L=OBros, P=TBDPS, A=COOCH$_3$) (198 mg, 93%) was obtained as a viscous oil.

IR (film): 2955, 1738, 1577, 1472, 1370, 1180, 947, 821, 703 cm$^{-1}$; $^1$H-NMR (500 MHz, CDCl$_3$): δ 7.71 (2H, d, J=8.8 Hz), 7.34–7.60 (12H, m), 4.87 (1H, m), 4.17 (1H, bs), 3.78 (3H, m), 2.98 (1H, dddd, J=9.1, 9.1, 3.5, 3.5 Hz), 2.39 (1H, d, J=11.9 Hz), 1.89 (1H, d, J=13.9 Hz), 1.79 (1H, d, J=12.3 Hz), 1.63 (1H, m), 1.34 (2H, m), 1.02 (9H, s), 0.91 (3H. s) ppm; MS (m/z): 599 (M$^+$, 1), 419 (28), 337 (34), 293 (8), 199 (46), 139, (100), 107 (50), 79 (72); [α]$_D^{25}$: +1.49 (c=1.75, CHCl$_3$).

f) (2S,3aS,4aS)-2-t-butyldiphenylsilyloxy-3a-carbomethoxy-bicyclo[3.1.0]hexane: I.b.4 (R=H, P=1TBDPS, A=COOCH$_3$).

As described for I.b.1 (R=H, P=TBDMS, A=COOCH$_3$), compound 2.8.b (R=H, L=OBros, P=TBDPS, A=COOCH$_3$) (206 mg, 0.344 mmol) was converted to I.b.4 (R=H, P=TBDMS, A=COOCH$_3$) (79 mg, 76%) obtained as a colorless oil.

IR (film): 2952, 1725, 1428, 1113, 703 cm$^{-1}$; $^1$H-NMR (500 MHz, CDCl$_3$): δ 7.64 (4H, dd, J=6.20, 6.20 Hz), 7.35–7.45 (6H, m), 3.89 (1H, dddd, J=7.7, 7.7, 7.7, 7.7 Hz), 3.65 (3H, s), 2.28 (1H, dd, J=12.9, 8.2 Hz), 2.12 (1H, dd, J=12.9, 7.1 Hz), 1.91 (2H, dd, J=8.6, 5.0, 5.0 Hz), 1.19 (1H, dd, J=8.6, 4.8 Hz), 1.02 (9H, s), 0.44 (1H, dd, J=5.1, 5.1 Hz) ppm; MS (m/z): 394 (M$^+$, 1), 363 (4), 337 (65), 259 (3), 213 (100), 199 (20), 135 (18), 77 (21); [α]$_D^{25}$: −73.14 (c=1.75, CHCl$_3$).

EXAMPLE 14

(2S,3aS,4aS)-2-t-butyliliphenylsilyloxy-3a-(hydroxymethyl)-bicyclo[3.1.0]hexane: I.b.5 (R=H, P=TBDPS, A=CH$_2$OH)

From I.b.4 (R=H, P=TBDPS, A=COOCH$_3$) (188 mg, 1.253 mmol) as described for I.b.2 (R=H, P=TBDMS, A=CH$_2$OH). Purification by flash chromatography on silica gel (isooctane/ethyl acetate 83:17) gsave I.b.5 (R=H, P=TBDPS, A=CH$_2$OH) (240 mg, 96%) as a viscous oil.

IR (film): 3322, 2932, 1428, 1113, 702 cm$^{-1}$; $^1$H-NMR (500 MHz, CDCl$_3$): δ 7.75 (4H, m), 7.58 (6H, m), 3.97 (1H, dddd, J=7.1, 7.1, 7.1, 7.1 Hz), 3.56 (2H, bs), 1.84–2.05 (3H, m), 1.12 (1H, m), 1.03 (9H, s), 0.34 (1H, dd, J=7.8, 5.4 Hz), 0.13 (1H, dd, J=4.6, 4.6 Hz) ppm; MS (m/z):365 (M$^+$−1, 1), 291 (3), 231 (10), 199 (100), 181 (12), 139 (27), 93 (77), 79 (24); [α]$_D^{25}$: −25.74 (c=2.16, CHCl$_3$).

EXAMPLE 15

(2S,3aS,4aS)-2-t-butyldiphenylsilyloxy-3a-formyl-bicyclo[3.1.0]hexane: I.b.6 (R=H, P=TBDPS, A=CHO)

From I.b.5 (R=H, P=TBDPS, A=CH$_2$OH) (230 mg, 0.627 mmol) as described for I.b.3 (R=H, P=TBDMS, A=CHO). The yield of I.b.6 (R=H, P=TBDPS, A=CHO) is 210 mg (92%).

IR (film): 3439, 3061, 2954, 2858, 1704, 1589, 1471, 1111, 1036, 823, 703 cm$^{-1}$; $^1$H-NMR (500 MHz, CDCl$_3$): δ 8.85 (1H, s), 7.68–7.60 (4H, m), 3.99 (1H, q, J=7.4 Hz), 2.30 (1H, dd, J=13.1, 8.0 Hz), 2.03–1.98 (2H, m), 1.93–1.87 (2H, m), 1.22 (1H, dd, J=8.4, 6.0 Hz), 1.02 (9H, s), 0.74 (1H, dd, J=5.3, 5.3 Hz) ppm; [α]$_D^{25}$: −90.00 (c 1.00, CHCl$_3$).

EXAMPLE 16

(2S,3aS,4aS)-2-t-butyldiphenylsilyloxy-3a-ethynyl-bicyclo[3.1.0]hexane: I.b.7 (R=H, P=TBDPS, A=C≡CH)

To a solution of (MeO)$_2$P(O)CHN$_2$ (188 mng, 1.253 mmol) in THF (3 ml) cooled to −78° C. was added dropwise t-BuOK (1.26 ml, 1.26 mmol, 1.0 M solution in THF). The mixture was stirred at −78° C. for 20 min. until the yellow color persisted. I.b.6 (R=H, P=TBDPS, A=CHO) (380 mg, 1.043 mmol) in THF (3 ml) was added slowly and stirring was continued overnight, the temperature raised naturally from −78° C. to room temperature. The reaction was quenched by the addition of water (10 ml) and Et$_2$O (20 ml) and the organic phase was separated, the aqueous layer was extracted with Et$_2$O (3×50 ml) and dried over MgSO$_4$. The residue was separated by HPLC (hexane/EtOAc 96:4), affording compound I.b.7 (R=H, P=TBDPS, A=C≡CH) (338 mg, 90%) as a colorless oil.

IR (film): 3291, 3072, 2932, 2143, 1590, 1473, 1428, 1114, 1091, 824, 741 cm$^{-1}$; $^1$H-NMR (500 MHz, CDCl$_3$): δ 7.61–7.63 (4H, m), 7.34–7.43 (6H, m), 3.81 (1H, q, J=7.6 Hz), 2.16 (1H, dd, J=12.5, 7.13 Hz), 2.02 (1H, ddd, J=12.5, 8.1, 0.9 Hz), 1.95 (1H, m), 1.93 (1H, s), 1.56 (1H, m), 1.02 (9H, s), 0.70 (1H, dd, J=8.3, 5.1 Hz), 0.31 1H, t, J=5.0 Hz) ppm; [α]$_D^{25}$: −86.30 (c=1.60, CHCl$_3$).

EXAMPLE 17

(2S,3aR,4aR)-2-t-butyldiphenylsilyloxy-3a-carbomethoxy-bicyclo[3.1.0]hexane: I.f.4 (R=H, P=TBDPS, A=COOCH₃)

a) Methyl (1R,3R,5S)-3-t-butyldiphenylsilyloxy-5-hydroxy-cyclohexane-carboxylate: 3.8.b (R=H, P=TBDPS, A=COOCH₃).

From 2.A (R=H, A=COOCH₃) and TBDPSCl, via 3.7.b (R=H, P=TBDPS, A=COOCH₃), as described for 3.8.a (R=H, P=TBDMS, A=COOCH₃) in Example 4. The title compound was obtained as a viscous oil; the yield for the two steps is 92%.

IR (film): 3404, 2952, 1738, 1428, 1112, 1049, 807, 710 cm⁻¹; ¹H-NMR (500 MHz, CDCl₃): δ 7.66 (4H, m), 7.40 (6H, m), 3.65 (3H; s), 3.60 (1H, dddd, J=10.9, 10.9, 4.3, 4.3 Hz), 3.41 (1H, m), 2.11 (4H, m), 1.50 (1H, dd, J=12.6, 12.6 Hz), 1.41 (1H, d, J=5.2 Hz), 1.34 (3H, m) ppm; MS (m/z): 412 (M⁺, 1), 355 (5), 323 (67), 199 (100), 153 (37), 105 (21), 79 (85); $[\alpha]_D^{25}$: −16.44 (c=1.60, CHCl₃).

b) Methyl (1S,3R,5S)-3-t-butyldiphenylsilyloxy-5-tosyloxy-cyclohexane-carboxylate: 3.6.b (R=H, L=OTos, P=TBDPS, A=COOCH₃).

From 3.8.b (R=H, P=TBDPS, A=COOCH₃) as described for 2.4.a (R=H, L=OTos, A=COOCH₃). 3.6 b is obtained as a viscous oil, 94% yield.

IR (film): 2955, 1738, 1363, 1178, 1111, 824, 704 cm⁻¹; ¹H-NMR (500 MHz, CDCl₃): δ 7.69 (2H, d, J=8.3 Hz), 7.58 (4H, m), 7.28 (2H, d, J=8.1 Hz), 4.18 (1H, dddd, J=11.6, 11.6, 4.6, 4.6 Hz) 3.62 (3H; s), 3.48 (1H, dddd, J=11.1, 11.1; 4.1, 4.1 Hz), 2.47 (3H, s), 2.15–1.99 (4H, m), 1.52 (1H, ddd, J=5.6, 5.57, 5.6 Hz), 1.42 (1H, ddd, J=12.0, 12.0, 12.0 Hz), 0.98 (9H, s) ppm; MS (m/z): 567 (M⁺, 1), 509 (9), 451 (1), 353 (49), 337 (67), 293 (38), 213 (47), 139 (32), 91 (100), 79 (77); $[\alpha]_D^{25}$: +2.39 (c=1.17, CHCl₃).

c) (2S,3aR,4aR)-2-t-butyidiphenylsilyloxy-3a-carbomethoxy-bicyclo[3.1.0]hexane: I.f4 (R=H, P=TBDPS, A=COOCH₃).

From 3.6.b (R=H, L=OBros, P=TBDPS, A=COOCH₃) as described for I.b.1 (R=H, P=TBDMS, A=COOCH₃). The yield is 81%.

IR (film): 3287, 2934, 1732, 1457, 1281, 1017 cm⁻¹; ¹H-NMR (500 MHz, CDCl₃): δ 3.73 (2H, m), 3.72 (3H; s), 2.53 (1H, dddd, J=12.2, 12.2, 3.4, 3.4 Hz), 2.26 (1H, d, J=11.3 Hz), 2.17 (2H, d, J=11.7 Hz), 1.30 (2H, ddd, J=12.0, 12.0, 12.0 Hz), 1.23 (1H, ddd, J=11.4, 11.4, 11.4 Hz) ppm; MS (m/z): 394 (M⁺, 1), 337 (31), 259 (5), 199 (55), 153 (48), 107 (100), 79 (52); $[\alpha]_D^{25}$: +31.97 (c=1.71, CHCl₃).

EXAMPLE 18

(2S,3aR,4aR)-2-t-butyidiphenylsilyloxy-3a-(hydroxymethyl)-bicyclo[3.1.0]hexane: I.f.5 (R=H, P=TBDPS, A=CH₂OH)

From I.f.4 (R=H, P=TBDPS, A=COOCH₃) as described for I.b.2 (R=H, P=TBDMS, A=CH₂OH). (2S,3aR,4aR)-2-t-butyldiphenylsilyloxy-3a-(hydroxymethyl)-bicyclo[3.1.0]hexane I.f.5 (R=H, P=TBDPS, A=CH₂OH) was obtained in 98% yield.

IR (film): 3332, 2931, 1428, 1111, 1008, 822, 702 cm⁻¹; ¹H-NMR (500 MHz, CDCl₃): δ 7.62 (4H, dd, J=7.9, 1.5 Hz), 7.39 (6H, m), 4.37 (1H, t, J=6.27 Hz), 3.57 (2H; s), 1.90–2.02 (3H, m), 1.80 (1H, d, J=13.8 Hz), 1.21 (1H, t, J=4.1 Hz), 1.15 (1H, m), 1.03 (9H, s), 0.60 (1H, m) ppm; MS (m/z): 365 (M⁺−1, 1), 291 (6), 231 (17), 199 (100), 181 (17), 139 (28), 93 (79), 79 (16); $[\alpha]_D^{25}$: +5.56 (c=1.5, CHCl₃).

EXAMPLE 19

(2S,3aR,4aR)-2-t-butyldiphenylsilyloxy-3a-formyl-bicyclo[3.1.0]hexane: I.f.6 (R=H, P=TBDPS, A=CHO)

From I.f.5 (R=H, P=TBDPS, A=CH₂OH) as described for I.b.3 (R=H, P=TBDMS, A=CHO). The yield is 96%.

IR (film): 2956, 1704, 1590, 1472, 1428, 1112, 1072, 822, 702 cm⁻¹; ¹H-NMR (500 MHz, CDCl₃): δ 8.85 (1H, s), 7.61 (4H, m), 7.43 (2H, dt, J=7.0, 1.0 Hz), 7.37 (4H, dt, J=7.0, 1.0 Hz), 4.40 (1H, t, J=6.0 Hz), 2.39 (1H, dd, J=14, 6.0 Hz), 1.89 (1H, d, J=13.0 Hz), 1.86 (1H, d, J=14.0 Hz), 1.53 (1H, m), 1.04 (9H, s) ppm; $[\alpha]_D^{25}$: +34.4 (c=1.6, CHCl₃).

EXAMPLE 20

(2S,3aR,4aR)-2-t-butyldiphenylsilyloxy-3a-ethynyl-bicyclo[3.1.0]hexane: I.f.7 (R=H, P=TBDPS, A=C≡CH)

From I.f.6 (R=H, P=TBDPS, A=CHO) as described for I.b.7 (R=H, P=TBDMS, A=C≡CH). The yield is 88%.

IR (film): 3310 (s), 3071, 2931, 2857, 2113, 1590, 1472, 1428, 1378, 1362, 1299, 1262, 1234, 1198, 1113, 1026, 933, 913, 865, 822, 701 cm⁻¹; ¹H-NMR (500 MHz, CDCl₃): δ 7.60 (4H, m), 7.42 (2H, td, J=2, 8 Hz), 7.37 (4H, td, J=1, 8 Hz), 4.32 (1H, m), 2.06 (2H, m), 2.04 (1H, dt, J=6, 14 Hz), 1.90 (1H, s), 1.80 (1H, d, J=14 Hz), 1.65 (1H, dt, J=5, 10 Hz), 1.49 (1H, t, J=5 Hz), 1.03 (9H, s), 1.03 (1H, m); $[\alpha]_D^{25}$: +21.4 (c=1.2, CHCl₃).

EXAMPLE 21

(2R,3aS,4aS)-2-t-butyldiphenylsilyloxy-3a-carbomethoxy-bicyclo[3.1.0]hexane: I.a.4 (R=H, P=IBDPS, A=COOCH₃)

a) Methyl (1R,3S,5R)-3-t-butyldiphenylsilyloxy-5-tosyloxy-cyclohexane-carboxylate: 2.3.b (R=H, L=OTos, P=TBDPS, A=COOCH₃).

From 2.5.a (R=H, L=OTos, A=COOCH₃) as described for 2.8.a (R=H, L=OTos, P=TBDMS, A=COOCH₂). The yield is 91%.

IR (film): 2932, 2857, 1736, 1428, 1364, 1177, 1107, 929, 822, 703, 665 cm⁻¹; ¹H-NMR (500 MHz, CDCl₃): δ 7.69 (2H, d, J=8.3 Hz), 7.57 (4H, dm, J=7 Hz), 7.44 (2H, q, J=7 Hz), 7.36 (4H, t, J=8 Hz), 7.28 (2H, d, J=8.4 Hz), 4.16 (1H, tt, J=4, 12 Hz), 3.63 (3H, s), 3.46 (1H, tt, J=4, 11 Hz), 2.43 (3H, s), 2.13 (1H, dm, J=12 Hz), 1.00 (9H, s) ppm; $[\alpha]_D^{25}$: −3.07 (c=1.04, CHCl₃).

b) (2R,3aS,4aS)-2-t-butyldiphenylsilyloxy-3a-carbomethoxy-bicyclo[3.1.0]hexane: I.a.4 (R=H, P=TBDPS, A=COOCH₃).

From 2.3.b (R=H, L=OTos, P=TBDPS, A=COOCH₃) as described for I.b.1 (R=H, P=TBDMS, A=COOCH₃). The yield is 75%.

IR (film): 2932, 2857, 1723, 1589, 1472, 1428, 1297, 1148, 1112, 1088, 702 cm⁻¹; ¹H-NMR (500 MHz, CDCl₃): δ 7.61 (4H, dd, J=1, 7 Hz), 7.42 (2H, t, J=7 Hz), 7.37 (4H, t, J=7 Hz), 4.36 (1H, t, J=6.1 Hz), 3.63 (3H, s), 2.37 (1H, ddd, J=1, 6.4, 14 Hz), 1.99 (1H, d, J=14 hz), 1.96 (1H, dd, J=6, 14 Hz), 1.87 (1H, dt, J=5, 9 Hz), 1.82 (1H, d, J=14 Hz), 1.63 (1H, dd, J=4, 5 Hz), 1.50 (1H, dm, J=9 Hz), 1.03 (9H, s) ppm; $[\alpha]_D^{25}$: −30.8 (c=0.46, CHCl₃).

EXAMPLE 22

(2R,3aS,4aS)-2-t-butyldiphenylsilyloxy-3a-(hydroxymethyl)-bicyclo[3.1.0]hexane: I.a.5 (R=H, P=TBDPS, A=CH₂OH)

From I.a.4 (R=H, P=TBDPS, A=COOCH₃) as described for I.b.2 (R=H, P=TBDMS, A=CH₂OH) in quantitative yield.

IR (film): 3346, 2930, 1589, 1472, 1428, 1111, 1092, 1076, 1031, 822, 701 cm⁻¹; ¹H-NMR (500 MHz, CDCl₃): δ

7.26 (4H, dd, J=1, 7 Hz), 7.41 (2H, t, J=7 Hz), 7.36 (4H, t, J=7 Hz), 4.38 (1H, t, J=6.3 Hz), 3.57 (2H, s), 2.00 (1H, dd, J=6, 13 Hz), 1.95 (1H, dd, J=7, 14 Hz), 1.92 (1H, d, J=14 Hz), 1.80 (1H, dd, J=14 Hz), 1.22 (2H, m), 1.15 (1H, m), 1.04 (9H, s), 0.60 (1H, m) ppm; $[\alpha]_D^{25}$: −5.6 (c=1.7, CHCl$_3$).

EXAMPLE 23

(2R,3aS,4aS)-2-t-butyldiphenylsilyloxy-3a-formyl-bicyclo[3.1.0]hexane: I.a.6 (R=H, P=TBDPS, A=CHO)

From I.a.5 (R=H, P=TBDPS, A=CH$_2$OH) as described for I.b3 (R=H, P=TBDMS, A=CHO). The yield is 93%.

IR (film): 2931, 1701, 1589, 1472, 1196, 1008, 822, 702 cm$^{-1}$; $^1$H-NMR (500 MHz, CDCl$_3$): δ 8.85 (1H, s), 7.61 (4H, m), 7.43 (2H, t, J=7 Hz), 7.37 (4H, t, J=7 Hz), 4.41 (1H, t, J=6 Hz), 2.39 (1H, dd, J=6, 14 Hz), 1.04 (9H, s) ppm; $[\alpha]_D^{25}$: −35.3 (c=1.6, CHCl$_3$).

EXAMPLE 24

(2R,3aR,4aR)-2-t-butyldiphenylsilyloxy-3a-carbomethoxy-bicyclo[3.1.0]hexane: I.h.4 (R=H, P=TBDPS, A=COOCH$_3$)

a) Methyl (1S,3S,5S)-3-t-butyldiphenyl-5-tosyloxy-cyclohexanecarboxylate: 3.13.b (R=H, L=OTos, P=TBDPS, A=COOCH$_3$).

From 3.12 (R=H, L=OTos, A=COOCH$_3$) (4.8 g, 14.63 mmol) as described for 2.8.a (R=H, L=OTos, P=TBDS, A=COOCH$_3$). The yield is 90%.

IR (film): 2954, 1731, 1272, 1176, 1107, 945, 813, 713, 664 cm$^{-1}$; $^1$H-NMR (500 MHz, CDCl$_3$): δ 7.53–7.25 (14H, m), 4.84 (1H, m), 3.68 (3H, s), 2.95 (1H, dt, J=3.3, 12.7 Hz), 2.45 (3H. s), 2.37 (1H, d, J=12.4 Hz), 1.84 (1H, d, J=12.7 Hz), 1.60 (1H, m), 1.29 (3H, m) ppm; MS (m/z): 566 (M$^+$), 477, 431, 399, 353, 283, 225, 198, 139, 91 (base peak); $[\alpha]_D^{25}$: +7.82 (c=1.31, CHCl$_3$).

b) (2R,3aR,4aR)-2-t-butyldiphenylsilyloxy-3a-carbomethoxy-bicyclo[3.1.0]hexane: I.h.4 (R=H, P=TBDPS, A=COOCH$_3$).

From 3.13.b (R=H, P=TBDPS, A=COOCH$_3$) (7.3 g, 12.89 mmol) as described for I.b.1 (R=H, P=TBDMS, A=COOCH$_3$). The yield is 79%.

IR (film): 2952, 2858, 1723, 1428, 1370, 1219, 1112, 823, 741, 702 cm$^{-1}$; $^1$H-NMR (500 MHz, CDCl$_3$): δ 7.66–7.38 (10H, m), 3.89 (1H, m), 3.65 (3H, s), 2.12 (1H, m), 1.92 (2H, m), 1.77 (1H, m), 1.14 (2H, m), 1.02 (9H, s), 0.45 (1H, m) ppm; MS (m/z): 394 (M$^+$), 393 (M$^+$−1), 363, 351, 337, 296, 259, 213 (base peak), 183, 135, 105, 77. $[\alpha]_D^{25}$: +72.58 (c=1.08, CHCl$_3$).

EXAMPLE 25

(2R,3aR,4aR)-2-t-butyldiphenylsilyloxy-3a-(hydroxymethyl)-bicyclo[3.1.0]hexane: I.h.5 (R=H, P=TBDPS, A=CH$_2$OH)

From I.h.4 (R=H, P=TBDPS, A=COOCH$_3$) as described for I.b.2 (R=H, P=TBDMS, A=CH$_2$OH). The yield is 98%.

IR (film): 3327, 2929, 2856, 1470, 1426, 1279, 1112, 1087, 1030, 822, 739, 700 cm$^{-1}$; $^1$H-NMR (500 MHz, CDCl$_3$): δ 7.65–7.35 (10H, m), 3.97 (1H, ddd, J=7.0, 7.2, 7.0), 3.55 (2H, bs), 2.04 (1H, m), 1.93 (1H, m), 1.87 (2H, m), 1.39 (1H, m), 1.02 (9H, s), 0.45 (1H, m), 0.13 (1H, m) ppm; MS (m/z): 365 (M$^+$−1), 322, 281, 237, 189 (base peak), 181, 139, 99, 77; $[\alpha]_D^{25}$: +24.77 (c=1.18, CHCl$_3$).

EXAMPLE 26

(2R,3aR,4aR)-2-t-butyldiphenylsilyloxy-3a-formyl-bicyclo[3.1.0]hexane: I.h.6 (R=H, P=TBDPS, A=CHO)

From I.h.5 (R=H, P=TBDPS, A=CH$_2$OH) as described for I.b3 (R=H, P=TBDMS, A=CHO).

IR (film): 2931, 2857, 1708, 1472, 1388, 1362, 1200, 1113, 1093, 1036, 901, 823, 742, 612 cm$^{-1}$; $^1$H-NMR (500 MHz, CDCl$_3$): δ 8.87 (1H, s), 7.65–7.35 (10H, m), 3.98 (1H, m), 2.29 (1H, dd, J=12.9, 8.1 Hz), 2.01 (2H, m), 1.89 (2H, m), 1.22 (1H, m), 1.02 (9H, s), 0.74 (1H, t, J=5.4 Hz) ppm; MS (m/z): 363 (M$^+$+1), 332, 307 (base peak), 289, 277, 263, 229, 211, 199, 181, 151, 139, 121,91,77,57,41; $[\alpha]_D^{25}$: +91.49 (c=0.47, CHCl$_3$).

EXAMPLE 27

(1R,2S,3aS,4aS)-3a-carbomethoxy-2-t-butyldiphenylsilyloxy-1-methyl-bicyclo[3.1.0] hexane I.a.7 (R=Me, P=TBDPS, A=COOCH$_3$)

a) Methyl (1S,3S,4R,5R)-3-t-butyldiphenylsilyloxy-4-methyl-5-acetoxy-cyclohexane 2.1.c (R=Me, P=TBDPS, A=COOCH$_3$)

To a stirred solution of 2'B (R=Me, A=COOCH$_3$) (0.81 g, 3.52 mmol), imidazole (0.72 g, 10.57 mmol, 99%) and DMAP (4-dimethylaminopyridine; 22 mg) in dry DMF (15 ml) was added dropwise TBDPSCl (1.8 ml, 7.04 mmol, 98%). The mixture was stirred for 20 h at room temperature. After completion, the reaction solution was poured into water-EtOAc (80 ml). The organic layer was separated and then the aqueous layer was extracted with EtOAc (50 ml×3). The combined extracts were washed with brine (3×10 ml), dried over MgSO$_4$ and concentrated to give a residue. The residue was purified by HPLC (isooctane/EtOAc 9:1), affording 2.1.c (R=Me, P=TBDPS, A=COOCH$_3$) (1.34 g, 84%).

$[\alpha]_D$=+9.9 (CHCl$_3$, c=0.65); $^1$H-NMR (500 MHz, in CDCl$_3$, ppm): 7.65–7.35 (10H, m), 4.59 (1H, dt, J=12.4, 4.5 Hz), 3.72 (1H, m), 3.62 (3H, s), 2.26 (1H, m), 2.09 (1H, m), 2.02 (3H, s), 1.81 (1H, dt, J=12.6, 4.1 Hz), 1.61 (1H, m), 1.08 (10H, s), 1.05 (3H, d, J=6.4 Hz). IR (film): 2954, 1737, 1428, 1364, 1239, 1111, 1037, 822, 740, 702 cm$^{-1}$; MS (m/z): 411 (M$^+$−57), 369, 351, 317, 291, 259, 258, 241, 199, 181, 135, 121, 93, 43 (base peak).

b) Methyl (1S,3S,4R,5R)-3-t-butyldiphenylsilyloxy-4-methyl-5-hydroxy-cyclohexane carboxylate 2.2.c (R=Me, P=TBDPS, A=COOCH$_3$)

To a stirred suspension of 2.1.c (R=Me, P=TBDPS, A=COOCH$_3$) (392 mg, 0.992 mmol) in 10 ml of dry MeOH at room temperature was added dry K$_2$CO$_3$ (30 mg). After 10 min., a second portion of K$_2$CO$_3$ (19 mg) (total: 49 mg, 0.496 mmol) was added. The mixture was stirred for 6 h, then poured into water and Et$_2$O (70 ml:50 ml). The organic layer was separated and the aqueous layer was extracted with Et$_2$O (50 ml×3) and dried over MgSO$_4$. Separation by flash chromatography on silica (isooctane/EtOAc) 9:1), gave hydroxy compound 2.2.c (R=Me, P=TBDPS, A=COOCH$_3$) (344 mg, 98%) as a colorless oil.

IR (film): 3448, 2954, 2858, 1737, 1654, 1472, 1362, 1279, 1240, 1173, 1008, 852, 822, 795, 741, 702, 611 cm$^{-1}$; $^1$H-NMR (500 MHz, in CDCl$_3$, ppm): 7.65 (4H, m), 7.44 (2H,m), 7.37 (4H, m), 3.69 (1H, m), 3.64 (3H, s), 3.51 (1H, m), 2.16 (1H, m), 2.08 (1H, m), 1.77 (1H, dt, J=12.6, 4.1 Hz), 1.69 (2H, t, J=8.9 Hz), 1.56 (1H, q, J=12.4 Hz), 1.37 (1H, d, J=5.3 Hz), 1.06 (9H, s), 1.02 (3H, d, J=7.0 Hz). MS (m/z): 337 (7), 309 (5), 291 (35), 199 (100), 156 (85), 181

(17), 153 (34), 121 (23), 93 (68), 57 (47). $[\alpha]_D^{25}$: +33.0 (c=0.54, CHCl$_3$).

c) Methyl (1S,3S,4R,5R)-3-tert-butyldiphenylsilyloxy-4-methyl-5-tosyloxy-cyclohexane carboxylate 2.3.c (R=Me, P=TBDPS, L=OTos, A=COOCH$_3$)

To a mixture of 2.2.c (R=Me, P=TBDMS, A=COOCH$_3$) (279 mg, 0.828 mmol), p-toluenesulfonyl chloride (323 mg, 1.69 mmol, 98%), DMAP (5.1 mg, 0.042 mmol) in 10 ml of dry CH$_2$Cl$_2$ at 0° C. (ice bath) was added Et$_3$N (308 μL, 2.54 mmol). The mixture was refluxed for three days; then p-toluenesulfonyl chloride (320 mg, 1.69 mmol, 98%), DMAP (5.1 mg, 0.042 mmol) and Et$_3$N (500 μL) were added. The resulting solution was refluxed for two days, p-toluenesulfonyl chloride (320 mg, 1.69 mmol, 98%), DMAP (5.1 mg, 0.042 mmol) and Et$_3$N (500 μL) were added again and reflux was continued for another day. The resulting mixture was diluted with 20 ml of CH$_2$Cl$_2$, washed with brine and the aqueous phase was extracted with EtOAc (4×50 ml). The combined organic phases were dried over MgSO$_4$. Filtration of the solvent, concentration and flash chromatography on silica (isooctane/EtOAc: 9:1), afforded 2.3.c (R=Me, P=TBDPS, L=OTos, A=COOCH$_3$) (316 mg, 83.5%) as a light yellow oil.

IR (film): 2954, 2858, 1737, 1365, 1246, 1177, 1106, 955, 704, 667 cm$^{-1}$; $^1$H-NMR (500 MHz, in CDCl$_3$, ppm): 7.71 (2H, d, J=8.3 Hz), 7.58 (4H, m), 7.43 (2H, m), 7.37 (4H, m), 7.31 (2H, d, J=8.1 Hz), 4.27 (1H, dt, J=12.0, 4.7 Hz), 3.61 (3H, s), 3.57 (1H, ddd, J=10.6, 5.1, 4.6 Hz), 2.45 (3H, s), 2.17 (1H, m), 2.01 (1H, m), 1.81 (1H, dt, J=12.8, 4.2 Hz), 1.74 (1H, dd, J=12.6 Hz), 1.64 (2H,m), 1.02 (9H, s), 0.99 (3H,d,J=6.6 Hz). MS (m/z): 523 (25), 507 (1), 463 (1), 409 (3), 353 (94), 307 (20), 293 (18), 213 (30), 199 (32), 135 (35), 91 (100), 77 (30). $[\alpha]_D^{25}$: −10.0 (c=1.22, CHCl$_3$).

d) (1R,2S,3aS,4aS)-3a-carbomethoxy-2-t-butyldiphenylsilyloxy-1-methyl-bicyclo[3.1.0]hexane I.a.7 (R=Me, P=TBDPS, A=COOCH$_3$)

To a solution of tosylate 2.3.c (R=Me, P=TBDPS, L=OTos, A=COOCH$_3$) (240 mg, 0.415 mmol) in a mixture of tert-BuOH (5 ml) and THF (2.8 ml) at 45° C. was added dropwise tert-BuOK (540 μL, 0.54 mmol, 1 M solution in tert-BuOH). The mixture was stirred for 1.5 h at 45° C., then poured into water and EtOAc (100 ml:50 ml). The organic phase was separated, the aqueous layer was extracted with EtOAc (3×50 ml) and dried over MgSO$_4$. The residue was separated by flash chromatography (isooctane/EtOAc: 100:2) affording compound I.a.7 (R=Me, P=TBDPS, A=COOCH$_3$) (122 mg, 72.0%) as a colorless oil.

IR (film): 2931, 1724, 1428, 1288, 1224, 1147, 1111, 1073, 1015, 933, 822, 740, 702, 609 cm$^{-1}$; $^1$H-NMR (500 MHz, in CDCl$_3$, ppm): 7.61 (14H, m), 7.42 (2H, m), 7.36 (4H, t, J=7.2 Hz), 4.19 (1H, t, J=6.0 Hz), 3.62 (3H, s), 2.30 (2H, m), 1.97 (1H, d, J=14.2 Hz), 1.85 (1H, m), 1.64 (1H, t, J=4.6 Hz), 1.35 (1H, dd, J=8.7, 3.9 Hz), 1.09 (9H, s), 0.99 (3H, d, J=6.9 Hz). MS (m/z): $[\alpha]_D^{25}$: −133.2 (c=1.61, CHCl$_3$).

EXAMPLE 28

(1R,2S,3aS,4aS)-3a-hydroxymethyl-2-t-butyldiphenyl-silyloxy-1-methyl-bicyclo3.1.0] hexanie I.a.8 (R=Me, P=TBDPS, A=CH$_2$OH)

To a solution of I.a.7 (R=Me, P=TBDPS, A=COOCH$_3$) (136 mg, 0.33 mmol) in THF (15 ml) at 0° C. was added dropwise LiAlH$_4$ (0.85 ml, 0.85 mmol, 1 M solution in THF). The resulting mixture was stirred at this temperature for 1.5 h, then water (0.1 ml) was added. The reaction mixture was filtered through Celite and was concentrated. The residue was purified by flash chromatography (silica gel: isooctane/EtOAc: 7:3) to afford I.a.8 (R=Me, P=TBDPS, A=CH$_2$OH) (124 mg, 97.8%) as a colorless oil.

IR (film): 3420, 2930, 1427, 1111, 1078, 1014, 701, 611, 504 cm$^{-1}$; $^1$H-NMR (500 MHz, in CDCl$_3$, ppm): 7.63 (4H, m), 7.42 (2H, m), 7.36 (4H, m), 4.21 (1H, t, J=6.0 Hz), 3.54 (1H, dd, J=11.4, 5.6 Hz), 3.50 (1H, dd, J=11.4, 5.6 Hz), 2.29 (1H, m), 1.95 (1H, ddd, J=13.7, 6.0, 1.4 Hz), 1.23 (1H, t, J=4.12 Hz), 1.14 (1H, m), 1.08 (9H, s), 0.99 (3H, d, J=7.0 Hz), 0.41 (1H, dd, J=8.4, 4.3 Hz), 0.80 (1H, m). MS (m/z): 381 (M$^+$+1, 1), 363 (22), 337 (1), 323 (22), 305 (5), 285 (9), 267 (24), 245 (63), 225 (19), 199 (83), 179 (19), 153 (29), 139 (51), 107 (100), 91 (58), 79 (72), 57 (86), 41 (78). $[\alpha]_D^{25}$: −2.6 (c=0.69, CHCl$_3$).

EXAMPLE 29

(1R, 2S, 3aS, 4aS)-3a-formyl-t-butyldiphenylsilyloxy-1-methyl-bicyclo[3.1.0] hexane I.a.9 (R=Me, P=TBDPS, A=CHO)

To a solution of (COCl)$_2$ (18 μL, 0.21 mmol) in CH$_2$Cl$_2$ (1.5 ml) at −78° C. was added dropwise DMSO (32 μL, 0.42 mmol) in CH$_2$Cl$_2$(100 μL). The mixture was stirred at −78° C. for 20 min., followed by the addition of alcohol I.a.8 (R=Me, P=TBDPS, A=CH$_2$OH) (40 mg, 0.105 mmol) in CH$_2$Cl$_2$ (1.5 ml). The resulting white suspension was stirred at −78° C. for 20 min. Then the mixture was allowed to warm to room temperature over 1 h. The reaction was quenched by the addition of cold water and the organic phase was separated, the aqueous layer was extracted with Et$_2$O (3×50 ml) and dried over MgSO$_4$. The residue was separated by HPLC (isooctane/EtOAc: 95:5), to afford compound I.a.9 (R=Me, P=TBDPS, A=CHO) (30 mg, 75%) as a colourless oil.

IR (film): 3420, 2930, 1427, 1111, 1078, 1014, 701, 611, 504 cm$^{-1}$; $^1$H-NMR (500 MHz, in CDCl$_3$, ppm): 8.80 (1H, s), 7.62 (4H, m), 7.42 (6H, m), 4.24 (1H, t, J=5.8 Hz), 2.32 (1H, dd, J=14.4, 6.1 Hz), 1.96 (2H, m), 1.84 (1H, d, J=14.4 Hz), 1.36 (1H, m), 1.08 (9H, s), 1.00 (3H, d, J=7.0 Hz), 0.91 (1H, d, J=6.8 Hz). MS (m/z): 378 (M$^+$, 1), 361 (4), 321 (100), 303 (10), 285 (10), 267 (24), 263 (16), 243 (74), 225 (39), 199 (100), 183 (76), 165 (39), 139 (72), 135 (48), 105 (59), 91 (34), 77 (60), 57 (95), 41 (80). $[\alpha]_D^{25}$=−16.2 (c=0.59, CHCl$_3$).

EXAMPLE 30

(1S,2R,3aR,4aR)-3a-carbomethoxy-2-tert-butyldiphenyl-silyloxy-1-methyl-bicyclo[3.1.0] hexane I.f.8 (R=Me, P=TBDPS, A=COOCH$_3$)

a) Methyl (1S,3S,4R,5R)-3-tosyloxy-4-methyl-5-acetoxy-cyclohexanecarboxylate 3.4.c (R=Me, L=OTos, A=COOCH$_3$)

From 2'B (R=Me, Z=Me, A=COOCH$_3$) (1.05 g, 4.57 mmol) as described for 2.3.c (R=Me, P=TBDPS, L=OTos, A=COOCH$_3$). The yield is 1.51 g, 89%.

IR (film): 2954, 1736, 1557, 1363, 1242, 1189, 1025, 956, 919, 667 cm$^{-1}$; $^1$H-NMR (500 MHz, in CDCl$_3$, ppm): 7.69 (2H, d, J=7.2 Hz), 7.38 (2H, d, J=7.2 Hz), 4.74 (1H, dt, J=12.2, 4.5 Hz), 4.49 (1H, dt, J=12.1, 4.7 Hz), 3.69 (3H, s), 2.46 (3H, s), 2.02 (3H, s), 1.98 (1H, dt, J=12.1, 4.7 Hz), 1.93 (1H, dt, J=12.6, 4.6 Hz), 1.81 (2H, dd, J=12.8 Hz), 1.63 (2H, dd, J=12.6 Hz), 0.97 (3H, d, J=6.9 Hz). MS (m/z): 384 (M$^+$), 343, 326, 311, 300, 269, 258, 213, 170, 152, 111, 93, 43 (base peak). $[\alpha]_D^{25}$=+51.1 (c=0.59, CHCl$_3$).

b) Methyl (1S,3S,4R,5R)-3-tosyloxy-4-methyl-5-hydroxycyclohexanecarboxylate 3.5.c (R=Me, L=OTos, A=COOCH$_3$)

From 3.4.c (R=Me, L=OTos, A=COOCH$_3$) as described for 2.2.c (R=Me, P=TBDPS, A=COOCH$_3$). The yield is 90%.

IR (film): 3439, 2988, 1732, 1439, 1353, 1176, 1097, 1021, 945, 667 cm$^{-1}$; $^1$H-NMR (500 MHz, in CDCl$_3$, ppm): 7.78 (2H, d, J=7.2 Hz), 7.32 (2H, d, J=7.2 Hz), 4.52 (1H, dt, J=10.8, 4.7 Hz), 3.69 (1H, m), 3.68 (3H, s), 2.45 (3H, s), 2.34 (1H, m), 2.25 (1H, m), 1.94 (2H, m), 1.87 (1H, dt, J=13.2, 4.5 Hz), 1.75 (1H, bs), 1.66 (1H, dd, J=11.9 Hz), 0.91 (3H, d, J=7.0 Hz). MS (m/z): 340 (M$^+$−2), 295, 278, 247, 220, 194, 170, 155, 127 (base peak), 91, 87, 57. [α]$_D^{25}$: +18.8 (c=0.41, CHCl$_3$).

c) Methyl (1S,3S,4R,5R)-3-tosyloxy-4-methyl-5-tert-butyldiphenylsilyloxy-cyclohexanecarboxylate 3.6.c (R=Me, L=OTos, P=TBDPS, A=COOCH$_3$)

From 3.5.c (R=Me, L=OTos, A=COOCH$_3$) as described for 2.1.c (R=Me, P=TBDPS, A=COOCH$_3$). The yield is 86%.

IR (film): 2955, 1736, 1598, 1427, 1363, 1177, 1031, 955, 914, 863, 820, 741, 703, 667 cm$^{-1}$; $^1$H-NMR (500 MHz, in CDCl$_3$, ppm): 7.69–7.38 (14H, m), 4.27 (1H, dt, J=12.1, 4.8 Hz), 3.61 (3H, s), 3.56 (1H, m), 2.44 (3H, s), 2.17 (1H, m), 2.02 (1H, m), 1.83 (1H, dt, J=12.5, 4.3 Hz), 1.73 (1H, dd, J=12.7 Hz), 1.63 (2H, m), 1.01 (9H, s), 0.99 (3H, d, J=7.2 Hz). MS (m/z): 523 (M$^+$−57), 463, 403, 353, 351, 293, 227, 213, 135, 91 (base peak), 77. [α]$_D^{25}$: −2.6 (c=0.94, CHCl$_3$).

d) (1S,2R,3aR,4aR)-3a-carbometlioxy-2-t-butyldiphenylsilyloxy-1-methyl-bicyclo[3.1.0]hexane I.f.8 (R=Me, P=TBDPS, A=COOCH$_3$)

From 3.6.c (R=Me, L=OTos, P=TBDPS, A=COOCH$_3$) as described for I.a.7 (R=Me, P=TBDPS, A=COOCH$_3$). The title compound is obtained in 68% yield as a colorless oil.

IR (film): 2931, 2857, 1724, 1428, 1367, 1288, 1223, 1147, 1111, 1073, 1015, 934, 822, 740, 702, 609 cm$^{-1}$; $^1$H-NMR (500 MHz, in CDCl$_3$, ppm): 7.62–7.31 (10H, m), 4.19 (1H, t, J=5.9 Hz), 3.59 (3H, s), 2.31 (2H, dd, J=13.7, 6.3 Hz), 1.96 (1H, d, J=14.5 Hz), 1.84 (1H, m), 1.64 (1H, t, J=4.6 Hz), 1.35 (1H, dd, J=12.8, 5.0 Hz), 1.25 (1H, br.), 1.07 (9H, s), 0.99 (3H, d, J=6.9 Hz), 0.91 (1H, m). MS (m/z): 408 (M$^+$), 351, 323, 273, 213, 199, 153, 121 (base peak), 77. [α]$_D^{25}$: +13.9 (c=0.65, CHCl$_3$).

EXAMPLE 31

(1S,2R,3aR,4aR)-3a-hydroxymethyl-2-t-butyldiphenylsilyloxy-1-methyl-bicyclo[3.1.0]hexane I.f.9 (R=Me, P=TBDPS, A=CH$_2$OH)

From I.f.8 (R=Me, P=TBDPS, A=COOCH$_3$) as described for I.a.8 (R=Me, P=TBDPS, A=CH$_2$OH). The yield is 98%.

IR (film): 3324, 2929, 2857, 1654, 1471, 1427, 1363, 1194, 1107, 1078, 1011, 822, 740, 701, 610 cm$^{-1}$. $^1$H-NMR (500 MHz, in CDCl$_3$, ppm): 7.68–7.37 (10H, m), 4.21 (1H, t, J=6.0 Hz), 3.54 (1H, dd, J=11.4, 6.0 Hz), 3.52 (1H, dd, J=11.4, 6.0 Hz), 2.29 (1H, dd, J=11.3, 8.1 Hz), 1.94 (1H, dd, J=14.6, 5.9 Hz), 1.86 (1H, d, J=13.2 Hz), 1.23 (1H, t, J=4.1 Hz), 1.14 (1H, m), 1.07 (9H, s), 0.99 (3H, d, J=6.9 Hz), 0.89 (1H, m), 0.41 (dd, J=8.1, 4.3 Hz). MS (m/z): 323 (M$^+$−57), 305, 267, 245, 199, 181, 139, 107. [α]$_D^{25}$: +3.1 (c=0.93, CH$_3$Cl).

EXAMPLE 32

(1S,2R,3aR,4aR)-3a-formyl-2-t-butyldiphenylsilyloxy-1-methyl-bicyclo[3.1.0]hexane I.f.10 (R=Me, P=TBDPS, A=CHO)

From I.f.9 (R=Me, P=TBDPS, A=CiJ$_2$OH) as described for I.a.9 (R=Me, P=TBDPS, A=CHO). The yield is 28%.

[α]$_D^{25}$: +15.8 (c=0.41, CH$_3$Cl); $^1$H-NMR (500 MHz, in CDCl$_3$, ppm): 8.80 (1H, s), 7.61–7.35 (10H, m), 4.24 (1H, t, J=5.8 Hz), 2.31 (2H, m), 1.96 (1H, m, dd, J=8.1, 5.9 Hz), 1.84 (1H, d, J=14.3 Hz), 1.37 (1H, dd, J=11.0, 7.1 Hz), 1.26 (1H, dd, J=9.7, 4.6 Hz), 1.07 (9H, s), 1.04 (3H, t, J=6.9 Hz). IR (film): 2959, 2857, 1703, 1471, 1391, 1383, 1274, 1215, 1191, 1111, 1109, 1009, 963, 823, 701 cm$^{-1}$. MS (m/z): 377 (M$^+$−1, 5), 337 (75), 321 (M$^+$−57, 8), 319 (10), 309 (10), 293 (6), 259 (12), 231 (20), 215 (16), 199 (100), 181 (30), 153 (20), 139 (60), 121 (95).

EXAMPLE 33

(1R,2S,3aS,4aS)-3a-carbomethoxy-2-t-butyldiphenylsilyloxy-1-ethyl-bicyclo[3.1.0]hexane I.a.10 (R=:Et, P=TBDPS, A=COOCH$_3$)

a) Methyl (1S,3S,4R,5R)-3-t-butyldiphenylsilyloxy-4-ethyl-5-acetoxy-cyclohexane 2.1.d (R=Et, P=TBDPS, A=COOCH$_3$)

From 2'C (R=Et, Z=Me, A=COOCH$_3$) as described for 3.4.c. The yield is 92%.

[α]$_D^{25}$: +7.5 (c=0.59, CH$_3$Cl); $^1$H-NMR (500 MHz, in CDCl$_3$, ppm): 7.45–7.36 (10H, m), 4.62 (1H, dt, J=12.2, 4.4 Hz), 3.69 (1H, dt, J=11.5, 4.3 Hz), 3.61 (3H, s), 2.08 (2H, tt, J=8.8, 3.9 Hz), 2.01 (3H, s), 1.85 (2H, m), 1.60 (3H, m), 1.51 (1H, m), 1.06 (9H, s), 1.02 (3H, t, J=7.5 Hz). IR (film): 2954, 2848, 1739, 1462, 1428, 1364, 1238, 1194, 1178, 1110, 1034, 986, 812, 740, 702 cm$^{-1}$. MS (m/z): 482 (M$^+$, 2), 468 (5), 451 (7), 425 (M$^+$−57), 391 (1), 365 (80), 351 (25), 305 (15), 273 (20), 241 (100), 213 (88), 199 (92), 153 (56), 135 (75), 107 (85).

b) Methyl (1S,3S,4R,5R)-3-t-butyldiphenylsilyloxy-4-ethyl-5-hydroxy-cyclohexanecarboxylate 2.2.d (R=Me, P=TBDPS, A=COOCH$_3$)

From 2.1.d (R=Et, P=TBDPS, A=COOCH$_3$) as described for 2.2.c (R=Me, P=TBDPS, A=COOCH$_3$). The yield is 98%.

[α]$_D^{25}$: +28.7 (c=0.19, CH$_3$Cl); $^1$H-NMR (500 MHz, in CDCl$_3$, ppm): 7.68 (10H, m), 3.68 (1H, dt, J=8.2, 4.2 Hz), 3.62 (3H, s), 3.57 (1H, dt, J=11.1, 4.6 Hz), 2.07 (1H, m), 1.85 (1H, t, J=4.1 Hz), 1.77 (1H, dt, J=8.6, 4.0 Hz), 1.71 (1H, tt, J=11.0, 4.0 Hz), 1.64 (2H, t, J=9.0), 1.59 (1H, overlap), 1.52 (1H, bs), 1.45 (1H, m), 1.06 (9H, s), 1.05 (3H, t, J=7.5). IR (film): 3435, 2995, 2858, 1736, 1589, 1460, 1427, 1363, 1271, 1236, 1172, 1111, 1050, 915, 875, 823, 740, 702, 647 cm$^{-1}$. MS (m/z): 383 (M$^+$−57, 14), 351 (16), 323 (18), 305 (90), 273 (18), 253 (10), 227 (50), 199 (100), 183 (70), 153 (80), 107 (98).

c) Methyl (1S,3S,4R,5R)-3-t-butyldiphenylsilyloxy-4-ethyl-5-tosyloxy-cyclohexanecarboxylate 2.3.d (R=Et, P=TBDPS, L=OTos, A=COOCH$_3$)

From 2.2.d (R=Et, P=TBDPS, A=COOCH$_3$) as described for 23.c (R=Me, P=TBDPS, L=OTos, A=COOCH$_3$). The yield is 82%.

[α]$_D^{25}$: −17.9 (c=0.59, CH$_3$Cl); $^1$H-NMR (500 MHz, in CDCl$_2$, ppm): 7.72–7.30 (14H, m), 4.28 (1H, dt, J=12.5, 4.5 Hz), 3.59 (3H, s), 3.55 (1H, dt, J=11.4, 4.3 Hz), 2.45 (3H, s), 1.96 (1H, tt, J=8.5, 4.1 Hz), 1.91 (1H, t, J=4.2 Hz), 1.84 (1H, dt, J=8.5, 4.1 Hz), 1.77 (1H, m), 1.73 (1H, m), 1.53 (2H, m), 1.47 (1H, m), 1.02 (9H, s), 0.97 (3H, t, J=7.5 Hz). IR (film): 2957, 2858, 1738, 1598, 14z87, 1462, 1428, 1360, 1277, 1189, 1111, 1030, 953, 885, 822, 741, 704 cm$^{-1}$;. MS (m/z): 357 (M$^+$−57, 45), 353 (100), 293 (22), 227 (5), 199 (48), 135 (70).

d) (1R,2S,3aS,4aS)-3a-carbomethoxy-2-t-butyldiphenylsilyloxy-1-ethyl-bicyclo[3.1.0]hexane I.a.10 (R=Et, P=TBDPS, A=COOCH$_3$)

From 2.3.d (R=Et, P=TBDPS, L=OTos, A=COOCH$_3$) as described for I.a.7 (R=Me, P=TBDPS, A=COOCH$_3$). The yield is 71%.

[α]$_D^{25}$: −33.3 (c=0.27, CH$_3$Cl); $^1$H-NMR (500 MHz, in CDCl$_3$, ppm): 7.63–7.35 (10H, m), 4.18 (1H, t, J=5.9 Hz), 3.61 (3H, s), 2.26 (1H, m), 2.06 (1H, m), 1.98 (1H, d, J=14.3 Hz), 1.92 (1H, m), 1.67 (1H, t, J=4.3 Hz), 1.48 (2H, m), 1.36 (1H, dd, J=8.7, 3.9 Hz), 1.05 (9H, s), 0.89 (3H, J=7.4 Hz). IR (film): 2958, 1723, 1427, 1366, 1298, 1224, 1148, 1111, 1064, 1028, 926, 821, 740, 610, 507 cm$^{-1}$. MS (m/z): 422 (M$^+$, 2), 391 (4), 365 (M$^+$−57, 40), 337 (8), 287 (12), 259 (10), 225 (8), 199 (65), 135 (100), 105 (38).

EXAMPLE 34

(1S,2R,3aR,4aR)-3a-carbomethoxy-2-t-butyldiphenylsilyloxy-1-ethyl-bicyclo[3.1.0]hexane I.f.11 (R=Et, P=TBDPS, A=COOCH$_3$)

a) Methyl (1S, 3S, 4R, 5R)-3-mesyloxy-4-ethyl-5-acetoxy-cyclohexane carboxylate 3.4.d (R=Et, L=OMs, A=COOCH$_3$).

To a solution of monoacetate 2'C (A=COOCH$_3$, R=Et, Z=Me) (0.1 g, 0.41 mmol), Et$_3$N (0.30 ml, 2.10 mmol) in 5 ml of CH$_2$Cl$_2$ was added dropwise MsCl (96 μL, 1.23 mmol) at room temperature. The resulting mixture was allowed to stir at room temperature for 10 h. The reaction solution was poured into ice-water, extracted with AcOEt (3×50 ml). The combined extracts were washed with brine (3×5 ml), dried over MgSO$_4$ and concentrated to give a residue. The residue was purified by HPLC eluting with isooctane/EtOAc (90:10) to give mesylate 3.4.d (A=COOCH$_3$, R=Et, L=OMs) (0.11 g, 85%).

IR (film): 2954, 1737, 1641, 1357, 1241, 1175, 952 cm$^{-1}$; $^1$H-NMR (500 MHz, in CDCl$_3$, ppm): 4.87 (1H, dt, J=10.9, 4.2 Hz), 4.75 (1H, dt, J=4.5, 10.9 Hz), 3.69 (3H, s), 3.00 (3H, s), 2.48 (1H, m), 2.23 (1H, bs), 2.13 (1H, dt, J=4.2, 11.8 Hz), 2.05 (3H, s), 2.01 (1H, d, J=8.8 Hz), 1.96 (1H, dt, J=13.3, 4.5 Hz), 1.83 (1H, m), 1.58 (2H, m), 1.01 (3H, s). MS (m/z): 322 (M$^+$), 309, 291, 248, 227, 199, 166, 135, 107, 78, 43 (base peak). [α]$_D^{25}$: +2.6 (c=1.08, CHCl$_3$).

b) Methyl (1S, 3S, 4R, 5R)-3-mesyloxy-4-ethyl-5-hydroxy-cyclohexanecarboxylate 3.5.d (A=COOCH$_3$, R=Et, L=OMs)

From 3.4.d (R=Et, L=OMs, A=COOCH$_3$) as described for 2.5.a (R=H, L=OTos, A=COOCH$_3$). The yield is 90%.

IR (film): 3439, 2957, 1729, 1438, 1351, 1277, 1174, 944, 877, 838, 757, 530 cm$^{-1}$; $^1$H-NMR (500 MHz, in CDCl$_3$, ppm): 4.87 (1H, t, J=3.1 Hz), 3.91 (1H, t, J=2.9 Hz), 3.74 (3H, s), 3.00 (3H, s), 2.69 (1H, bs), 2.44 (1H, bs), 2.17 (1H, bs), 2.00 (2H, m), 1.84 (2H, dt, J=14.3, 4.7 Hz), 1.71 (2H, m), 1.03 (3H, t, J=7.4 Hz). MS (m/z): 281 (M$^+$+1), 263, 249, 236, 200, 184, 166, 141, 125, 111, 87, 78, 55 (base peak). [α]$_D^{25}$: +51.3 (c=0.61, CHCl$_3$).

c) Methyl (1S, 3S, 4R, 5R)-3-mesyloxy-4-ethyl-5-t-butyldiphenylsilyloxy-cyclohexanecarboxylate 3.6.d (R=Et, L=OMs, P=TBDPS, A=COOCH$_3$)

From 3.5.d (R=Et, L=OMs, A=COOCH$_3$) as described for 2.8.a (R=H, L=OTos, P=TBDPS, A=COOCH$_3$). The yield is 86%.

IR (film): 2957, 2857, 1738, 1588, 1462, 1427, 1358, 1276, 1177, 1111, 1030, 949, 885, 823, 741, 703, 614 cm$^{-1}$; $^1$H-NMR (500 MHz, in CDCl$_3$, ppm): 7.65–7.35 (10H, m), 4.44 (1H, dt, J=12.2, 4.6 Hz), 3.67 (1H, dt, J=11.6, 4.2 Hz), 3.63 (3H, s), 2.79 (3H, s), 2.09 (1H, dt, J=12.9, 3.9 Hz), 2.06 (1H, m), 2.02 (2H, m), 1.85 (1H, m), 1.79 (1H, dd, J=12.8 Hz), 1.65, 1H, dt, J=13.1, 4.0 Hz), 1.49 (1H, m), 1.06 (9H, s), 1.04 (3H, t, J=7.5 Hz). MS (m/z): 461 (M$^+$−57), 401, 365, 351, 305, 277, 231, 199, 167, 135, 107 (base peak). [α]$_D^{25}$: −2.3 (c=0.35, CHCl$_3$).

d) (1S, 2R,3aR, 4aR)-3a-carbomethoxy-2-t-butyldiphenylsilyloxy-1-ethyl-bicyclo[3.1.0]hexane I.f.11 (R=Et, P=TBDPS, A=COOCH$_3$).

From 3.6.d (R=Et, L=OMs, P=TBDPS, A=COOCH$_3$) as described for I.a.7 (R=Me, P=TBDPS, A=COOCH$_3$). The yield is 71%. IR (film): 2958, 1723, 1427, 1366, 1298, 1224, 1148, 1111, 1064, 1028, 926, 821, 740, 610, 507 cm$^{-1}$. $^1$H-NMR (500 MHz, in CDCl$_3$, ppm): 7.63–7.35 (10H, m), 4.18 (1H, t, J=5.9 Hz), 3.61 (3H, s), 2.26 (1H, m), 2.06 (1H, m), 1.98 (1H, d, J=14.3 Hz), 1.92 (1H, m), 1.67 (1H, t, J=4.3 Hz), 1.48 (2H, m), 1.36 (1H, dd, J=8.7, 3.9 Hz), 1.05 (9H, s), 0.89 (3H, J=7.4 Hz). MS (m/z): 422 (M$^+$, 2), 391 (4), 365 (M$^+$−57, 40), 337 (8), 287 (12), 259 (10), 225 (8), 199 (65), 135 (100), 105 (38). [α]$_D^{25}$: +28.4 (c=0.75, CHCl$_3$).

EXAMPLE 35

(1R,2S,3aR,4aR)-3a-carbomethoxy-2-t-butyldiphenylsilyloxy-1-methyl-bicyclo[3.1.0] hexane I.e.1 (R=Me, P=TBDPS, A=COOCH$_3$)

a) Methyl (1S, 3S, 4R, 5S)-3-t-butyldiphenylsilyloxy-4-methyl-5-hydroxy-cyclohexane carboxylate 3.2.c (R=Me, P=TBDPS, A=COOCH$_3$).

To a solution of 2.2.c (R=Me, P=TBDPS, A=COOCH$_3$) (167 mg, 0.392 mmol), picolinic acid (257 mg, 2.092 mmol) and triphenylphosphine (548 mg, 2.092 mmol) in THF at −38° C. was added dropwise DIAD (diisopropyl azodicarboxylate; 412 μL, 2.092 mmol) over 4 min. The reaction solution was stirred for 4.5 h and warmed to room temperature overnight. The mixture was poured into water and EtOAc (50 ml:50 ml). The organic phase was separated, the aqueous layer was extracted with EtOAc (3×50 ml) and dried over MgSO$_4$. The residue was separated by HPLC (isooctane/EtOAc 98:2), affording (4S,6S)-4-carbomethoxy-6-t-butyldiphenylsilyloxy-1-methylcyclohexene (142 mg, 88.8%) as a colorless oil.

IR (film): 2953, 2856, 1738, 1428, 1247, 1168, 1111, 1068, 999, 893, 820, 741, 702, 614 cm$^{-1}$. $^1$H-NMR (500 MHz, in CDCl$_3$, ppm): 7.71 (4H, m), 7.43 (2H, m), 7.38 (4H, m), 5.39 (1H, m), 4.25 (1H, bs), 3.60 (3H, s), 2.39 (1H, m), 2.19 (1H, m), 2.13 (1H, m), 2.04 (1H, m), 1.75 (1H, dd, J=22.3, 12.5 Hz), 1.66 (3H, bs), 1.08 (9H, s). MS (m/z): 387 (1), 361 (1), 351 (75), 319 (5), 273 (5), 273 (5), 213 (100), 183 (70), 137 (65), 105 (30), 77 (85). [α]$_D^{25}$: +81.9 (c=1.91, CHCl$_3$).

To a stirred solution of this cyclohexene (110 mg, 0.27 mmol) in 2 ml of diglyme at 0° C. was added dropwise a borane-THF complex solution (1.0 M, 325 μL, 0.325 mmol, 1.5 eq). The resulting solution was stirred for 4 h at 0° C. THF was removed and TAO (trimethyl amine N-oxide, 90 mg, 0.81 mmol) was added. The mixture was heated and refluxed for 2 h. The resulting mixture was cooled to room temperature, extracted with EtOAc (4×40 ml) and dried over MgSO$_4$. The residue was separated by flash chromatography on silica, then was purified by HPLC (Cyclohexane/EtOAc: 9:1) to afford compound 3.2.c (R=Me, P=TBDPS, A=COOCH$_3$) (46 g, 40.5%) as a colorless oil.

IR (film, cm$^{-1}$): 3453, 2954, 2858, 1737, 1462, 1428, 1379, 1272, 1195, 1111, 1032, 934, 823, 702. $^1$H-NMR (500 MHz, in CDCl$_3$, ppm): 7.66 (4H, m), 7.42 (2H, m), 7.38 (4H, m), 4.17 (1H, dt, J=10.7, 4.7 Hz), 3.88 (1H, bs), 3.62 (3H, s), 2.61 (1H, m), 1.85~1.65 (5H, m), 1.06 (9H, s), 0.96 (3H, d, J=7.2 Hz). [α]$_D^{25}$: +39.4 (c=0.95, CHCl$_3$).

b) Methyl (1S,3S,4R,5S)-3-t-butyldiphenylsilyloxy-5-mesyloxy-4-methyl-cyclohexanecarboxylate 3.3.c (R=Me, L=OMs, P=TBDPS, A=COOCH$_3$)

From 3.2.c (R=Me, P=TBDPS, A=COOCH$_3$) as described for 3.4.d (R=Et, L=OMs, A=COOCH$_3$). The yield is 84.5%

IR (film): 2952, 1732, 1470, 1427, 1357, 1275, 1177, 1112, 1029, 929, 904 cm$^{-1}$. $^1$H-NMR (500 MHz, in CDCl$_3$, ppm): 7.65 (4H, t, J=8.0 Hz), 7.40 (6H, m), 4.80 (1H, bs), 4.06 (1H, m), 3.65 (3H, s), 2.70 (3H, s), 2.58 (1H, m), 2.04 (1H, bs), 1.98~1.76 (4H, m), 1.06 (9H, s), 1.03 (3H, d, J=7.2 Hz). $[\alpha]_D^{25}$: +30.3 (c=0.52, CHCl$_3$).

c) (1R,2S,3aR,4aR)-3a-carbomethoxy-2-t-butyldiphenylsilyloxy-1-methyl-bicyclo[3.1.0]hexane I.e.1 (R=Me, P=TBDPS, A=COOCH$_3$)

From 3.3.c (R=Me, L=OMs, P=TBDPS, A=COOCH$_3$) as described for 1.a.7 (R=Me, P=TBDPS, A=COOCH$_3$). The yield is 68.8%.

IR (film): 2951, 1725, 1428, 1259, 1238, 1111, 880, 814, 742, 702 cm$^{-1}$. $^1$H-NMR (500 MHz, in CDCl$_3$, ppm): 7.63 (4H, m), 7.45~7.35 (6H, m), 3.84 (1H, m), 3.64 (3H, s), 2.23 (1H, m), 2.02 (1H, m), 1.93 (1H, m), 1.60 (1H, m), 1.17 (1H, m), 1.04 (12H, bs), 0.56 (1H, m).

EXAMPLE 36

(2R,3aS,4aS)-2-methyl-2-hydroxy-3a-hydroxymethyl-bicyclo[3.1.0] hexane: I.i.1 (A= CH$_2$OH, R$_1$=Me: scheme 4)

a) (2R,3aS,4aS)-2-hydroxy-3a-[(benzoyloxy)methyl]-bicyclo[3.1.0]hexane: 4.1

To a solution of I.a.5 (R=H, P=TBDPS, A=CH$_2$OH) (4.451 g, 12.15 mmol), DMAP (250 mg, 2.27 mmol) and Et$_3$N (16.5 ml, 121.1 mmol) in CH$_2$Cl$_2$ (50 ml) at 0° C. was added dropwise benzoyl chloride. The mixture was stirred for 22 h at room temperature, the solution was diluted with 70 ml of CH$_2$Cl$_2$. The organic phase was separated, washed with brine (3×100 ml) and dried over MgSO$_4$. The residue was purified by flash chromatography (silica gel, isooctane/EtOAc: 100:2.5), affording the corresponding benzoate (5.51 g, 96.5%) as a colorless oil. To a solution of this benzoate (2.22 g, 4.72 mmol) in THF (40 ml) was added TBAF (14 ml, 14 mmol, 1M in THF), and the resulting solution was stirred at room temperature for 14 h. The solvent was evaporated under vacuum. The residue was passed through a short silica gel column (isooctane/EtOAc: 7:3). The crude product was purified by HPLC (isooctane/EtOAc: 7:3), affording compound 4.1 (1.03 g, 94.0%) as a colorless oil.

IR (film): 3413.8, 2928.3, 1714.1, 1602.1, 1452.1, 1277.5, 1115.1, 1070.0, 958.3, 808.3, 711.5 cm$^{-1}$. $^1$H-NMR (500 MHz, in CDCl$_3$, ppm): 8.06 (2H, d, J=7.8 Hz), 7.56 (1H, t, J=7.3 Hz), 7.45 (1H, t, J=7.7 Hz), 4.48 (1H, m), 4.34 (2H, dd, J=19.4, 11.5 Hz), 2.23 (2H, m), 1.94 (1H, d, J=14.0 Hz), 1.78 (1H, d, J=14.2 Hz), 1.38 (1H, ddd, J=8.3, 4.3, 4.3 Hz), 1.30 (1H, bs), 1.06 (1H, t, J=4.4 Hz), 0.75 (1H, m) MS (m/z): 232 (M$^+$, 1), 214 (1), 199 (1), 189 (1), 161 (1), 149 (1), 110 (13), 105 (100), 77 (43). 67 (14). $[\alpha]_D^{25}$: -27.96 (c=1.47, CHCl$_3$).

b) (3aS,4aS)-3a-[(benzoyloxy)methyl-]-bicyclo[3,1,0]hexane-2-one: 4.2

To a solution of alcohol 4.1 (209 mg, 0.904 mmol) in CH$_2$Cl$_2$ (30 ml) was added pyridinium dichromate (PDC, 1.072 g, 4.97 mmol), and the mixture was stirred at room temperature for 16 h. The resulting solution was directly purified by flash chromatography (silica gel column 3×15 cm) (isooctane/EtOAc: 9:1 to 8:2), affording compound 4.2 (197 mg, 95%) as a colorless oil.

IR (film): 1745.0, 1715.9, 1451.2, 1355.4, 1272.1, 1155.7, 1111.3, 1069.9, 711.0 cm$^{-1}$. $^1$H-NMR (500 MHz, in CDCl$_3$, ppm): 8.05 (2H, d, J=8.9 Hz), 7.58 (1H, t, J=7.4 Hz), 7.46 (2H, t, J=7.6 Hz), 4.41 (1H, dd, J=29.6, 12.7 Hz), 2.75 (2H, m), 2.41 (1H, d, J=9.0 Hz), 2.28 (1H, d, J=9.3 Hz), 1.68 (1H, m), 1.10 (1H, t, J=7.0 Hz), 0.37 (1H, t, J=5.1 Hz). MS (m/z): 230 (M$^+$, 1), 212 (1), 202 (6.9), 183 (1), 161 (1), 149 (1), 106 (13), 105 (100), 77 (46), 51 (20). $[\alpha]_D^{25}$: -36.50 (c=4.07, CHCl$_3$).

c) (2R,3aS,4aS)-2-methyl-2-hydroxy-3a-hydroxymethyl-bicyclo[3.1.0]hexane I.i.1 (R$_1$=Me, A=CH$_2$OH)

To a solution of ketone 4.2 (120 mg, 0.52 mmol) in THF (4 ml) was added dropwise a solution of MeMgBr in Et$_2$O (1.5 ml, 3.0 M) over 5 min at −78° C. The resulting mixture was stirred for 6 h at this temperature, then allowed to warm to room temperature overnight. A saturated NH$_4$Cl aqueous-ice solution (0.2 ml) was added to quench the reaction. The mixture was passed through a short silica gel column including MgSO$_4$. The residue was separated by HPLC (isooctane/EtOAc: 5:5), affording compound I.i.1 (R$_1$=Me, A=CH$_2$OH) (55 mg, 74%) as a white solid.

IR (film):: 3288.4, 2931.3, 2858.5, 1459.1, 1370.2, 1260.7, 1183.9, 1135.7,1111.5, 1064.0, 1016.0, 922.6 cm$^{-1}$. $^1$H-NMR (500 MHz, in CDCl$_3$, ppm): 3.58 (2H, s), 2.08 (1H, d, J=13.7 Hz), 2.03 (1H, dd, J=13.8, 5.0 Hz), 1.88 (1H, d, J=13.7 Hz), 1.76 (1H, d, J=13.8 Hz), 1.34 (3H, s), 1.29 (1H, bs), 1.21 (1H, m), 1.14 (1H, t, J=4.3 Hz), 1.11 (1H, s), 0.57 (1H, dd, J=8.4, 4.5 Hz). MS (m/z): 124 (2), 109 (6), 93 (12), 81 (12), 71 (10), 67 (10), 55 (11), 43 (100). $[\alpha]_D^{25}$: -33.10 (c=1.17, MeOH).

EXAMPLE 37

(2R,3aS,4aS)-2-methyl-2-hydroxy-3a-formyl-bicyclo[3.1.0]hexane I.i.2 (R$_1$=Me, A=CHO)

To a solution of SO$_3$-pyridine complex (2.5 eq, 140 mg) in DMSO:CH$_2$Cl$_2$ (500 μL:250 μL) and Et$_3$N (2.5 eq, 120 μL), a solution of I.i.1 (R$_1$=Me, A=CH$_2$OH) (1 eq, 50 mg, 35 μmol) in DMSO: CH$_2$Cl$_2$ (500 μL:250 μL) and Et$_3$N (2.5 eq, 120 μL) was added at −15° C. After stirring for 1 h at −10° C. to −5° C. the mixture was poured into Et,O: brine. The organic layer was dried (MgSO$_4$). After evaporation of the solvent, the residue was purified by column chromatography (Et$_2$O:isooctane 1:1 to Et$_2$O:isooctane: methanol: CH$_2$Cl$_2$ 100:100:1:20) affording I.i.2 (R$_1$=Me, A=CHO) as a colorless oil (37 mg, 75%).

IR (film): 3441, 2929, 1694, 1435, 1258, 1105, 1049, 963, 893 cm$^{-1}$; $^1$H-NMR (500 MHz, in CDCl$_3$, ppm): 8.81 (1H, s), 2.47 (1H, d, J=14 Hz), 2.03 (2H, m), 1.91 (1H, t, J=5 Hz), 1.88 (1H, d, J=13 Hz), 1.81 (1H, d, J=14 Hz), 1.49 (1H, ddt, J=9,5, 1 Hz), 1.36 (3H, s). $[\alpha]_D^{25}$: -79.7 (c=1.22, CHCl$_3$).

EXAMPLE 38

(2R,3aS,4aS)-2-ethyl-2-hydroxy-3a-hydroxymethyl-bicyclo[3.1.0]hexane I.i.3 (A=CH$_2$OH, R$_1$=Et) (Scheme 4)

From 4.2 as described for I.i.1 (R$_1$=Me, A=CH$_2$OH). The yield is 66.6%.

IR (film):: 3275.4, 2921.3, 2858.5, 1431.8, 1284.3, 1237.3, 1122.3, 1068.0, 1027.8, 930.7 cm$^{-1}$; $^1$H-NMR (500 MHz, in CDCl$_3$, ppm): 3.59 (2H, d, J=5.6 Hz), 2.03 (1H, d, J=13.6 Hz), 1.99 (1H, dd, J=13.9, 4.9 Hz), 1.83 (1H, d, J=13.7 Hz), 1.72 (1H, d, J=13.8 Hz), 1.55 (2H, q, J=6.4), 1.23 (2H, m), 1.16 (1H, t, J=4.2 Hz), 1.04 (1H, s), 0.92 (3H, t, 7.4 Hz), 0.54 (1H, dd, J=8.4, 4.3 Hz). MS (m/z): 138 (2), 123 (4), 109 (12.9), 97 (2), 91 (6), 79 (20), 72 (6), 67 (12.9), 57 (100), 43 (8). $[\alpha]_D^{25}$: -34.90 (c=0.928, MeOH).

EXAMPLE 39

(2R,3aS,4aS)-2-ethyl-2-hydroxy-3a-formyl-bicyclo[3.1.0]hexane I.i.4 (A=CHO, R$_1$=Et)

From I.i.3 (R$_1$=Et, A=CH$_2$OH) as described for I.i.2 (R$_1$=Me, A=CHO). The yield is 50%.

IR (film): 3418, 2966, 1689, 1114, 1057, 982, 632 cm$^{-1}$; $^1$H-NMR (500 MHz, in CDCl$_3$, ppm): 8.80 (1H, s), 2.09 (2H, m), 1.92 (1H, t, J=5.0 Hz), 1.83 (1H, d, J=13.3 Hz), 1.69 (1H, d, J=10.0 Hz), 1.57 (2H, m), 1.49 (1H, m), 1.15 (1H, s), 0.93 (3H, t, J=7.4 Hz). [α]$_D^{25}$: −68.1 (c=0.30, CHCl$_3$).

EXAMPLE 40

(2R,3aS,4aS)-2-[(t-butyldiphenylsilyloxy)-methyl]-3a-hydroxymethyl-bicyclo[3.1.0]hexane I.j.1 (A=CH$_2$OH, P=TBDPS) (Scheme 4)

a/(3aS,4aS)-2-methylene-3a-[(benzoyloxy)methyl]-bicyclo[3.1.0]hexane 4.3

To a stirred suspension of zinc dust (5.75 g) in CH$_2$Br$_2$ (2.02 ml) and THF (40 ml) at −78° C. was added dropwise TiCl$_4$ over 10 min. The mixture was allowed to warm to 8° C. and stirred at this temperature for 72 h to give a thick gray slurry of the active species (Lombardo reagent).

To a solution of ketone 4.2 (98 mg, 0.426 mmol) in CH$_2$Cl$_2$ (8 ml) was added by portions the Lombardo reagent at room temperature, until the ketone disappeared (TLC). The reaction mixture was diluted with Et$_2$O (40 ml), saturated NaHCO$_3$ was added, and stirring was continued for 30 min, giving two clear phases. The aqueous phase was extracted with Et$_2$O (3×25 ml) and CH$_2$Cl$_2$ (2×25 ml). The combined organic phases were dried with MgSO$_4$. The residue was purified by flash chromatography (silica gel: pentane/ether: 100:1), affording compound 4.3 (66 mg, 67.9%) as a colorless oil.

IR (film): 2925.8, 1715.6, 1451.5, 1269.7, 1111.0, 1069.0, 1026.1, 741.9, 710.7 cm$^{-1}$. $^1$H-NMR (500 MHz, in CDCl$_3$, ppm): 8.07 (2H, d, J=7.3 Hz), 7.56 (1H, t, J=7.4 Hz), 7.45 (2H, t, J=7.7 Hz), 4.81 (2H, d, J=12.4 Hz), 4.38 (2H, s), 2.68 (2H, m), 2.43 (1H, d, J=15.4 Hz), 2.28 (1H, d, J=15.6 Hz), 1.36 (1H, m), 0.68 (1H, t, J=6.5 Hz), 0.39 (1H, t, J=4.5 Hz). MS (m/z): 228 (M$^+$, 1), 213 (1), 199 (1), 181 (2), 169 (1), 141 (1), 123 (5), 105 (100), 91 (88), 77 (57), 65 (7), 51 (20). [α]$_D^{25}$: −51.90 (c=1.73, CHCl$_3$).

b) (2R,3aS,4aS)-2-[(t-butyldiphenylsilyloxy)-methyl]-3a-hydroxymethyl-bicyclo[3.1.0]hexane I.j.1 (A=CH$_2$OH, P=TBDPS) and (2S,3aS,4aS)-2-[(t-butyldiphenylsilyloxy)-methyl]-3a-hydroxymethyl-bicyclo[3.1.0]hexane I.k.1 (A=CH$_2$OH, P=TBDPS)

To a solution of alkene 4.3 (49 mg, 0.21 mmol) in THF (6 ml) at −5° C. was added BH$_3$.THF and the reaction mixture was stirred at this temperature for 3.5 h. The reaction was quenched with saturated aqueous NaHCO$_3$ (3.9 ml) and H$_2$O$_2$ (30%) (3.9 ml). The reaction solution was allowed to warm to room temperature and was stirred for 1.5 h. Then the solution was extracted with Et$_2$O (2×20 ml) and EtOAc (2×20 ml). The combined organic layers were dried on MgSO$_4$ and concentrated. The residue was passed through a short silica gel column, the crude product was purified by HPLC (isooctane/EtOAc: 7:3), affording a mixture of epimeric hydroxylated products (2R:2S; ratio, 75:25, 39 mg, 73.7%) as a colorless oil.

To a solution of this mixture (35 mg, 0.142 mmol), imidazole (49 mg, 0.720 mmol, 5 eq.) and DMAP (7.8 mg, 0.064 mmol, 0.45 eq.) in DMF (3 ml) was added dropwise TBDPSCl at −0° C.; the resulting mixture was stirred at room temperature for 19 h. The reaction solution was poured into Et$_2$O/water (50 ml/40 ml), and the aqueous phase was extracted with Et$_2$O (3×20 ml) and EtOAc (2×20 ml). The combined organic layers was dried over MgSO$_4$ and concentrated. The residue was purified by flash chromatography (silica gel, isooctane/EtOAc: 100:2), affording the corresponding silylethers (56 mg, 81.3%) as a colorless oil.

To a stirred solution of this mixture (50 mg, 0.106 mmol) in MeOH (6 ml including 0.2 ml H$_2$O) at room temperature was added K$_2$CO$_3$ (50 mg, 0.505 mmol). The mixture was stirred for 20 h at room temperature, the solid was filtered off, the filtrate was diluted with Et$_2$O (50 ml), washed with brine (2×20 ml), and dried over MgSO$_4$, and the solvent was evaporated. The residue was passed through a short silica gel column and separation by HPLC (isooctane/EtOAc: 75:25), afforded compounds I.j.1 (A=CH$_2$OH, P=TBDPS) (24 mg, 61.8%) and I.k.1 (A=CH$_2$OH, P=TBDPS) (8 mg, 20.4%) as colorless oils.

MS (m/z): 379 (M$^+$−1, 1), 305 (1), 275 (2), 229 (2), 199 (47), 181 (7), 107 (100), 79 (53).

Compound I.j.1 (A=CH$_2$OH, P=TBDPS)

IR (film): 3342.5, 2930.3, 2858.0, 1471.8, 1427.7, 1389.8, 1111.9, 1008.2, 823.7, 739.7, 701.6 cm$^{-1}$. $^1$H-NMR (500 MHz, in CDCl$_3$, ppm): 7.64 (4H, d, J=7.8 Hz), 7.45~7.35 (6H, m), 3.54 (2H, dd, J=14.4, 11.2 Hz), 3.41(2H, d, J=7.4 Hz), 2.61 (1H, m), 2.19~2.09 (2H, m), 1.64 (1H, dd, J=13.5, 4.8 Hz), 1.47 (1H, dd, J=13.6, 4.6 Hz), 1.26 (1H, bs), 1.18 (1H, dt, J=8.6, 4.3, 4.3 Hz), 1.02 (9H, s), 0.62 (1H, dd, J=8.4, 4.7 Hz), 0.35 (1H, t, J=4.4 Hz). [α]$_D^{25}$: −13.05 (c=1.40, CHCl$_3$).

Compound I.k.1 (A=CH$_2$OH, P=TBDPS)

IR (film): 3342.5, 2929.9, 2856.7, 1471.6, 1427.7, 1388.8, 1111.9, 1086.1, 1031.5, 1008.5, 823.7, 739.3, 701.5 cm$^{-1}$. $^1$H-NMR (500 MHz, in CDCl$_3$, ppm): 7.64 (4H, d, J=6.7 Hz), 7.39 (6H, m), 3.64 (1H, d, J=11.2 Hz), 3.57 (3H, d, J=7.8 Hz), 1.97~1.87 (2H, m), 1.80 (1H, dd, J=12.3, 7.0 Hz), 1.56 (2H, m), 1.22 (1H, m), 1.15 (1H, ddd, J=8.3, 4.1, 4.1 Hz), 1.02 (9H, s), 0.52 (1H, t, J=4.3 Hz), 0.41 (1H, dd, J=8.0, 5.0 Hz). [α]$_D^{25}$: −6.16 (c=1.65, CHCl$_3$).

EXAMPLE 41

(2R,3aS,4aS)-2-[(t-biityldiphenylsilyloxy)-methyl]-3a-formyl-bicyclo[3.1.0]hexane I.j.2 (A=CHO, P=TBDPS) (Scheme 4)

To a solution of (COCl)$_2$ (30 μL, 0.344 mniol) in CH$_2$Cl$_2$ (1 ml) at −78° C. was added dropwise DMSO (36.6 μL, 0.515 mmol) in CH$_2$Cl$_2$ (100 μL). The mixture was stirred at −78° C. for 20 min., followed by the addition of I.j.1 (A=CH$_2$OH, P=TBDPS) (14 mg, 0.37 mmol) in CH$_2$Cl$_2$ (0.5 ml). The resulting white suspension was stirred at −78° C. for 20 min., Et$_3$N (0.2 ml, 1.435 mmol) was added dropwise and stirring was continued for 20 min. Then, the mixture was allowed to warm to room temperature over 1 h. The reaction was quenched by the addition of cold water and the organic phase was separated, the aqueous layer was extracted with Et$_2$O (3×50 ml) and dried over MgSO$_4$. The residue was separated by HPLC (hexane/EtOAc 95:5), to afford compound I.j.2 (A=CHO, P=TBDPS) (4 mg, 28.7%) as a colorless oil.

IR (film): 2931, 2858, 1699, 1428, 1112, 824, 740, 613 cm$^{-1}$;. $^1$H-NMR (500 MHz, in CDCl$_3$, ppm): 8.83 (1H, s), 7.63 (4H, d, J=7.4 Hz), 7.68–7.35 (6H, m), 3.43 (2H, d, J=5.5 Hz), 2.68 (2H, m), 2.18 (1H, m), 2.02 (1H, m), 1.59 (1H, m), 1.51 (1H, d, J=8.0 Hz), 1.25 (1H, bs), 1.02 (9H, s), 0.90 (1H, m). MS (m/z): 337 (4), 307 (2), 293 (4), 259 (2), 217 (9), 199 (54), 183 (20), 135 (24), 105 (30), 93 (100); [α]$_D^{25}$: −52.6 (c=0.27, CHCl$_3$).

EXAMPLE 42

(2S,3aS,4aS)-2-[(t-butyldiphenylsilyloxy)-methyl]-3a-formyl-bicyclo[3.1.0]hexane I.k.2 (A=CHO, P=OTBDPS) (Scheme 4)

From I.k.1 (A=CH$_2$OH, P=TBDPS) as described for I.j.2 (A=CHO, P=TBDPS). The yield is 92.8%.

IR (film): 2932, 2858, 1703, 1471, 1427, 1112, 824, 741, 702 cm$^{-1}$;. $^1$H-NMR (500 MHz, in CDCl$_3$, ppm): 8.96 (1H, s), 7.63 (4H, m), 7.48–7.35 (6H, m), 3.58 (2H, m), 2.05–1.88 (5H, m), 1.62 (1H, m), 1.34 (1H, dd, J=8.5, 5.5 Hz), 1.20 (1H, t, J=5.4 Hz), 1.02 (9H, s). MS (m/z): 337 (15), 259 (14), 231 (30), 199 (100), 137 (20), 93 (60), 77 (70).

EXAMPLE 43

(2S,3aS,4aS)-2-methyl-2-hydroxy-3a-hydroxymethyl-bicyclo[3.1.0]hexane I.l.1 (A=CH$_2$OH, R$_1$=CH$_3$) (Scheme 4)

To a solution of Hg(OAc)$_2$ (350 mg, 1.10 mmol) in water (1.5 ml) was added dropwise a solution of olefin 4.3 (164 mg, 0.719 mmol) in THF (1.5 ml). After stirring the mixture for 30 min at room temperature, an aqueous NaOH solution (1.5 ml, 3N), followed by 0.5M NaBH$_4$ in 3N NaOH solution (1.5 ml) were added. The resulting mixture was stirred for 2 h at room temperature until most of the mercury had coagulated. The solid was filtered off. The filtrate was extracted with Et$_2$O (2×30 ml) and EtOAc (2×30 ml). To the residue was added K$_2$CO$_3$ (500 mg, 5.05 mmol) and MeOH (2 ml). The mixture was stirred for 20 h at room temperature. The reaction mixture was passed a short silica-gel column. The crude product was purified by HPLC (cyclohexane/EtOAc: 62:45), affording compounds I.l.1 (A=CH$_2$OH, R$_1$=Me) and I.i.1 (A=CH$_2$OH, R$_1$=Me) (ratio: 3:1, 68 mg, 66.6%) as a colorless oil.

IR (film):: 3288.4, 2931.3, 2858.5, 1459.1, 1370.2, 1260.7, 1183.9, 1135.7,1111.5, 1064.0, 1016.0, 922.6 cm$^{-1}$. $^1$H-NMR (500 MHz, in CDCl$_3$, ppm): 4.02 (1H, d, J=10.7 Hz), 3.07 (1H, d, J=10.7 Hz), 2.05 (2H, m), 1.65 (1H, bs), 1.52 (1H, d, J=12.8 Hz), 1.37 (3H, m), 1.25 (3H, s), 1.05 (1H, dd, J=8.0, 4.8 Hz), 0.49 (1H, t, J=4.3 Hz).

EXAMPLE 44

(2S,3aS,4aS)-2-methyl-2-hydroxy-3a-formyl-bicyclo[3.1.0]hexane 1.1.2 (A=CHO, R$_1$=Me) (Scheme 4)

From I.l.1 (A=CH$_2$OH, R$_1$=Me) as described for I.j.2 (A=CHO, P=TBDPS). The yield is 48.2%.

IR (film): 3429, 2967, 2929, 1691, 1377, 1249, 1102, 1036, 668 cm$^{-1}$. $^1$H-NMR (500 MHz, in CDCl$_3$, ppm): 8.90 (1H, s), 2.66 (1H, dd, J=14.3, 2.4 Hz), 1.98 (2H, m), 1.88 (1H, dd, J=8.5, 5.2 Hz), 1.65 (1H, bs), 1.51 (2H, t, J=14.2 Hz), 1.31 (3H, s), 1.14, (1H, t, J=5.2 Hz). MS (m/z): 140 (M$^+$, 2), 123 (10), 111 (10), 97 (15), 85 (25), 71 (25), 67 (30), 48 (100). [α]$_D^{25}$: −99.3 (c=1.06, CHCl$_3$).

EXAMPLE 45

(2S,3aS,4aS)-2-hydroxy-2-hydroxymethyl-3a-[(benzoyloxy)methyl]-bicyclo[3.1.0]hexane I.m (A=CH$_2$OCOPh) (Scheme 4)

To a solution of 4.3 (65 mg, 0.285 mmol) and NMO (48 mg, 0.344 mmol, 1.21 eq) in acetone/water (5 ml:2.5 ml), an OsO$_4$ aqueous solution (121 μl, 0.02 mmol, 4 wt %, 0.07 eq) was added at 0° C. The resulting solution was stirred for 39 h at room temperature, then sodium dithionite (70 mg) and Florisil (150 mg) were added. The black precipitate was removed by filtration and washed with Et$_2$O (200 ml). The solvent was evaporated under vacuum. The residue was dissolved in Et$_2$O containing a small amount of acetone (100:5) and filtered over Florisil. The crude mixture was separated by HPLC (cyclohexane/EtOAc: 7:3), affording compound I.m next to the C-2 epimer as the minor product (ratio 85.15) in 64% combined yield as colorless oils.

IR (film):: 3385.5, 2927.8, 1713.7, 1451.6, 1315.2, 1274.6, 1114.7, 1070.3, 1026.2, 934.5, 711.5 cm$^{-1}$. $^1$H-NMR (500 MHz, in CDCl$_3$, ppm): 8.06 (2H, d, J=7.3 Hz), 7.57 (1H, t, J=7.4 Hz), 7.46 (2H, t, J=7.6 Hz), 4.48 (1H, d, J=11.5 Hz), 4.21 (1H, d, J=11.5 Hz), 3.49 (2H, m), 2.58 (1H, s), 2.36 (1H, s), 2.16 (1H, d, J=14.6 Hz), 2.12 (1H, dd, J=14.2, 6.3 Hz), 1.94 (1H, t, J=14.1 Hz), 1.89 (1H, t, J=14.1 Hz), 1.65 (1H, d, J=14.2 Hz), 1.07 (1H, dd, J=8.4, 5.3 Hz), 0.47 (1H, t, J=4.6 Hz). MS (m/z): 262 (M$^+$, 1), 244 (1), 232 (3), 213 (4), 203 (3), 176 (1), 163 (4), 145 (4), 123 (16), 105 (100), 77 (52), 67 (13). [α]$_D^{25}$: −11.86 (c=1.53, CHCl$_3$).

What is claimed is:

1. A method of preparing a compound of formula (I):

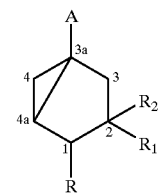

(I)

in which:

A is a group —CH$_2$OH, —CH$_2$—OCOR', —COR", —CSR" or an ethynyl;

R is hydrogen or a (C$_1$–C$_6$)alkyl;

R$_1$ is hydrogen, a (C$_1$–C$_6$)alkyl or a group —(CH2)$_n$—OP;

R$_2$ is hydrogen or a group —OP;

R' is a (C$_1$–C$_6$)alkyl or a phenyl;

R" is hydrogen, a hydroxyl, a (C$_1$–C$_6$)alkyl, a (C$_1$–C$_6$) alkoxy, a (C$_1$–C$_6$)alkylthio, or a di(C$_1$–C$_3$)alkylamino;

P is hydrogen; a (C$_1$–C$_6$)alkanoyl; a benzoyl in which the phenyl is optionally substituted by a (C$_1$–C$_4$)alkyl, a halogen or a nitro; a (C$_1$–C$_6$)alkoxycarbonyl; a group —Si(R$_3$)$_3$ in which each R$_3$ independently represents a (C$_1$–C$_6$)alkyl or a phenyl; a mono- or di-(C$_1$–C$_6$)alkoxy (C$_1$–C$_6$)alkyl; a tetrahydrofuranyl; or a tetrahydropyranyl;

n is 0, 1, 2, 3 or 4, which method comprises the steps of (i) reacting a compound of formula 1

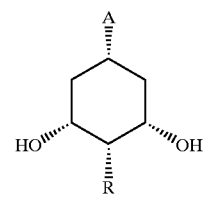

1 in which A is a (C$_1$–C$_6$)alkoxycarbonyl or a di(C$_1$–C$_3$) alkylaminocarbonyl and R is as defined above, with a lipase in a vinylalkanoate or an acid anhydride, and (ii) converting the resulting compound of formula 2 or 2'

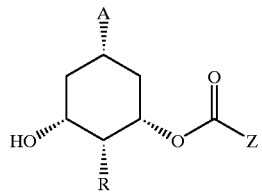
2

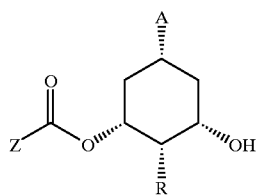
2' in which Z is an alkyl, to the corresponding compound of formula (I).

2. The method according to claim 1 which comprises reacting a compound 1 in which A is a methoxycarbonyl.

3. The method according to claim 1 wherein the vinylalkanoate is selected from the group consisting of vinylacetate, vinylpropionate and vinylbutyrate.

4. The method according to claim 1 wherein the acid anhydride is selected from the group consisting of acetic anhydride, propionic anhydride and butyric anhydride.

5. The method according to claim 1 wherein the lipase is selected from the group consisting of SAM II, PPL, CCL, PSL and GCL.

6. The method according to claim 1 wherein step (i) is carried out at a temperature in the range of 10 to 40° C.

7. The method according to claim 1 wherein step (i) is carried out for 6 to 72 h.

8. The method according to claim 1 wherein step (ii) is carried out via one or several of each of the following steps:
protection of hydroxy groups,
ester saponification,
inversion of a 3- or 5-hydroxy group,
formation of a leaving group,
ring closure to form the desired bicyclo[3.1.0]hexane,
conversion of the carboalkoxy or carbamoyl function to the desired substituent A.

9. The method according to claim 1, wherein Z is a $(C_1-C_3)$alkyl.

* * * * *